(12) United States Patent
Salbeck et al.

(10) Patent No.: US 6,211,369 B1
(45) Date of Patent: Apr. 3, 2001

(54) SPIRO COMPOUNDS AND THE USE THEREOF

(75) Inventors: Josef Salbeck, Kelkheim; Donald Lupo, Frankfurt, both of (DE)

(73) Assignee: Aventis Research & Technologies GmbH & Co. KG, Frankfurt am Main (DE)

( * ) Notice: Subject to any disclaimer, the term of this patent is extended or adjusted under 35 U.S.C. 154(b) by 0 days.

(21) Appl. No.: 09/381,317

(22) PCT Filed: Mar. 18, 1998

(86) PCT No.: PCT/EP98/01589

§ 371 Date: Jan. 3, 2000

§ 102(e) Date: Jan. 3, 2000

(87) PCT Pub. No.: WO98/42715

PCT Pub. Date: Oct. 1, 1998

(30) Foreign Application Priority Data

Mar. 20, 1997 (DE) .............................................. 197 11 568

(51) Int. Cl.$^7$ ................................................. C07D 471/00
(52) U.S. Cl. ................. 546/18; 546/14; 546/15; 546/16; 546/85; 549/4; 549/31; 549/43; 136/263
(58) Field of Search .................. 549/31, 4, 43; 546/15, 18, 14, 85, 16; 136/263

(56) References Cited

U.S. PATENT DOCUMENTS

| 5,084,365 | 1/1992 | Gratzel et al. ........................ 429/111 |
| 5,683,833 | 11/1997 | Haussling et al. .................... 429/192 |
| 5,840,217 | 11/1998 | Lupo et al. .......................... 252/583 |
| 5,885,368 | 3/1999 | Lupo et al. .......................... 136/263 |

FOREIGN PATENT DOCUMENTS

| 0 333 641 A1 | 9/1989 | (EP) . |
| 0 676 461 A2 | 10/1995 | (EP) . |
| 0 718 858 A2 | 6/1996 | (EP) . |
| WO 97/10617 | 3/1997 | (WO) . |

OTHER PUBLICATIONS

Abstract No. XP–002073521 (1970).
Abstract No. XP–002073522 (1970).

*Primary Examiner*—Amelia Owens
(74) *Attorney, Agent, or Firm*—Frommer Lawrence & Haug LLP

(57) ABSTRACT

Spiro compounds of the formula (I),

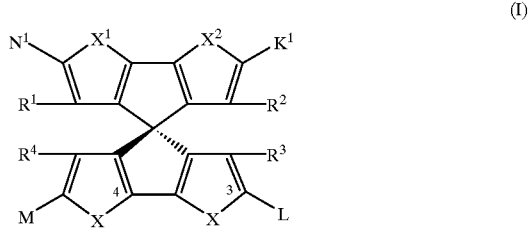

where $X^1$, $X^2$, $X^3$, $X^4$ are identical or different and are —S—, —O—, —$NR^5$—, —$CR^5$=N— or —$CR^5$=CH—, with the proviso that at least one of the groups $X^{1-4}$ is different from —$CR^5$=CH—, are suitable as charge transport materials, in particular for photovoltaic cells, and as electroluminescence materials.

5 Claims, 1 Drawing Sheet

SPIRO COMPOUNDS AND THE USE THEREOF

Figure 1:
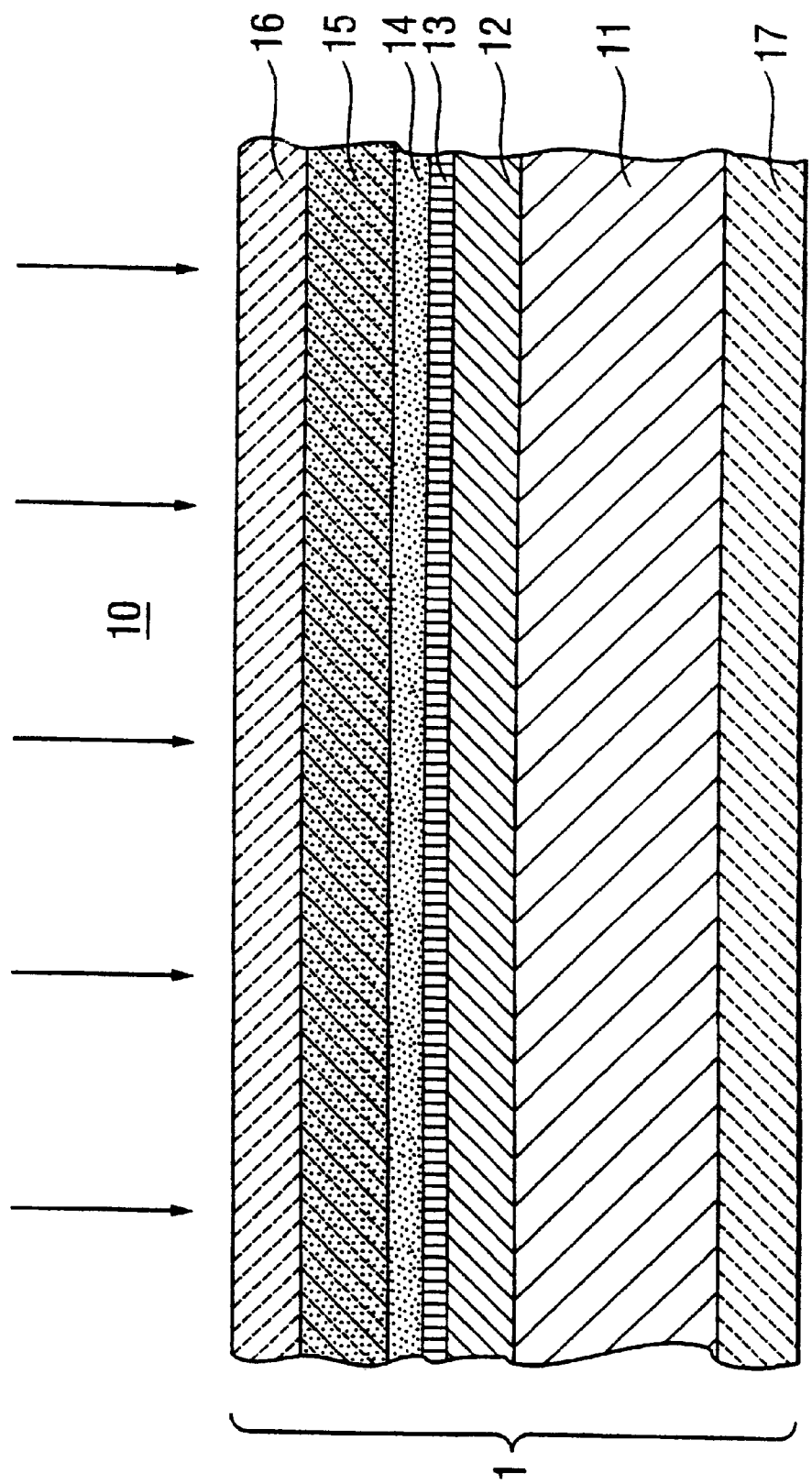

Owing to the rising global demand for electric energy and the limited reserves of coal, oil and gas, which in addition liberate the greenhouse gas $CO_2$ when they are burnt, the generation of electric power from sunlight has attracted increased interest in recent years.

EP-A 0 333 641 describes a photoelectrochemical cell which comprises a nanoporous metal oxide semiconductor, i.e. a semiconductor which has an extremely roughened surface and thus has an increased surface area. The charge transport between semiconductor/chromophore layer and counterelectrode in this cell occurs via an electrolyte solution. Although good results are achieved with such cells, the property profile of such a device is still capable of significant improvement.

EP-A 0 718 858 discloses such a cell having a liquid crystal charge transport material in place of an electrolyte. The apparent quantum yields achieved are, however, still in need of improvement.

It has now surprisingly been found that certain spiro compounds are very suitable as charge transport materials for photovoltaic cells.

Some structurally different spirobifluorene derivatives are described, for example, in U.S. Pat. No. 5,026,894, J. M. Tour et al. J. Am. Chem. Soc. 112 (1990) 5662 and J. M. Tour et al. Polym. Prepr. (1990) 408 as coupling elements for polymeric, organic semiconductors and are proposed as materials for molecular electronics.

EP-A 0 676 461 describes the use of spiro compounds of the following formula

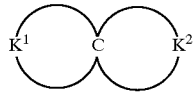

where $K^1$ and $K^2$ are, independently of one another, conjugated systems, in electroluminescence devices.

Use in photovoltaic cells cannot be deduced therefrom.

SUMMARY OF THE INVENTION

The invention accordingly provides spiro compounds of the formula (I),

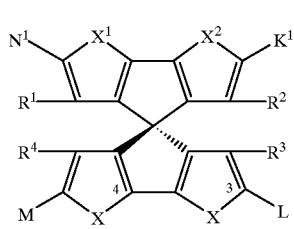

(I)

where the symbols have the following meanings:
$X^1$, $X^2$, $X^3$, $X^4$ are identical or different and are —S—, —O—, —$NR^5$—, —$CR^5$=N—, —$CR^5$=CH—, with the proviso that at least one of the groups $X^{1-4}$ is different from —$CR^5$=CH—;
$K^1$, L, M, $N^1$, $R^1$, $R^2$, $R^3$, $R^4$ are identical or different and are each a) hydrogen, —$NO_2$, —CN, —F or —Cl, b) a straight-chain or branched alkyl radical having from 1 to 20 carbon atoms, where
  b1) one or more nonadjacent $CH_2$ groups can be replaced by —O—, —S—, —CO—O—, —O—CO—, —O—CO—O—, $NR^5$ or —Si$(CH_3)_2$— and/or
  b2) one or more $CH_2$ groups can be replaced by —CH=CH—, —C≡C—, 1,4-phenylene, 1,4-cyclohexylene or 1,3-cyclopentylene and/or
  b3) one or more H atoms can be replaced by F and/or Cl and/or c) one of the following groups:

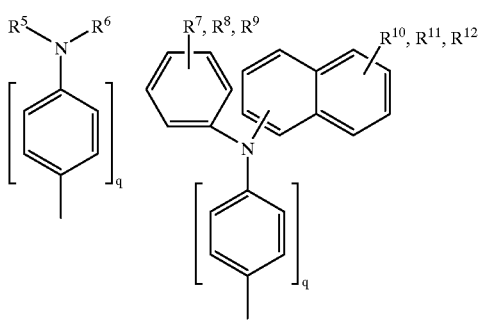

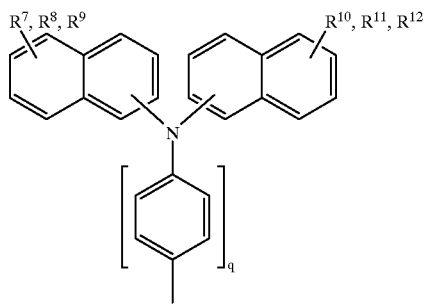

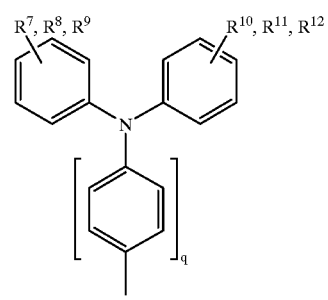

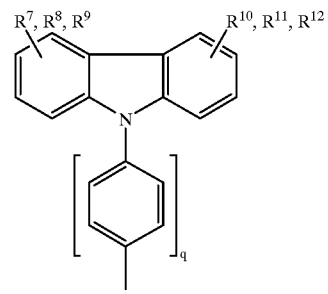

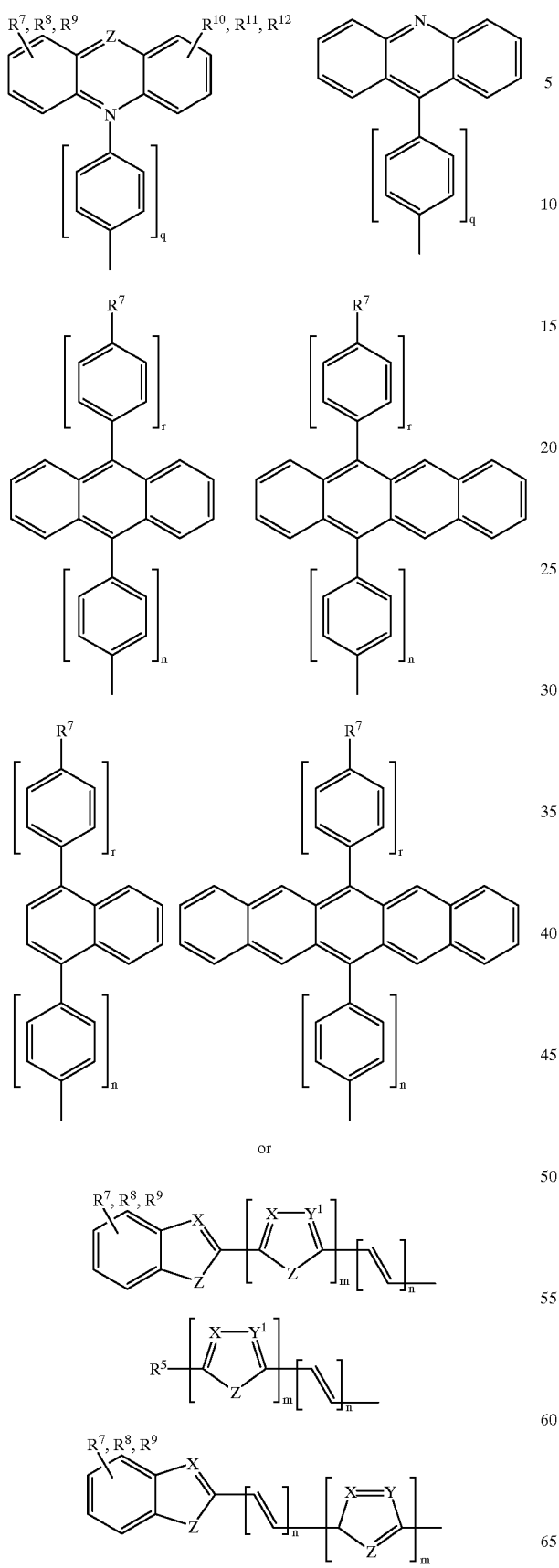
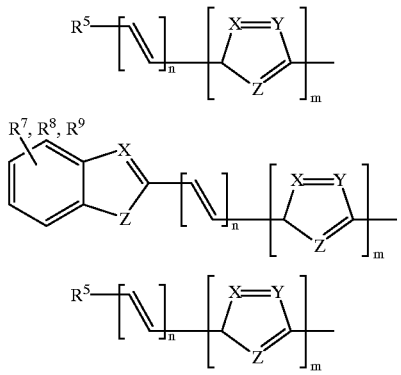

X, Y¹ are in each case identical or different and are =CR⁷— or =N—;

Z is —O—, —S—, —NR⁵—, —CRR—, —CR=CR— or —CR=N—;

R⁵, R⁶ are in each case identical or different and are each
a) hydrogen
b) a straight-chain or branched alkyl radical having from 1 to 20 carbon atoms, where
  b1) one or more nonadjacent CH₂ groups which are not bound to nitrogen can be replaced by —O—, —S—, —CO—O—, —O—CO—, —O—CO—O— or —Si(CH₃)₂ and/or
  b2) one or more CH₂ groups can be replaced by —CH=CH—, —C≡C—, cyclopropane-1,2-diyl, 1,4-phenylene, 1,4-cyclohexylene or 1,3-cyclopentylene and/or
  b3) one or more H atoms can be replaced by F and/or Cl and/or
  b4) R⁵ and R⁶ together can also form a ring;
c) phenyl, biphenyl, 1-naphthyl, 2-naphthyl, 2-thienyl, 2-furanyl;

R⁷, R⁸, R⁹, R¹⁰, R¹¹, R¹² are identical or different and are each
a) hydrogen, —CN, —F, NO₂ or —Cl
b) a straight-chain or branched alkyl radical having from 1 to 20 carbon atoms, where
  b1) one or more nonadjacent CH₂ groups can be replaced by —O—, —S—, —CO—O—, —O—CO—, —O—CO—O—, —NR⁵ or —Si(CH₃)₂— and/or
  b2) one or more CH₂ groups can be replaced by —CH=CH—, —C≡C—, cyclopropane-1,2-diyl, 1,4-phenylene, 1,4-cyclohexylene or 1,3-cyclopentylene and/or
  b3) one or more H atoms can be replaced by F and/or Cl;
c) phenyl, biphenyl, 1-naphthyl, 2-naphthyl, 2-thienyl, 2-furanyl, —O-phenyl, —O-biphenyl, —O-1-naphthyl, —O-2-naphthyl, —O-2-thienyl, —O-2-furanyl, m, n, p, q, r are in each case identical or different and are 0, 1, 2, 3, 4, 5 or 6, preferably 0, 1, 2, 3, 4, particularly preferably 0, 1, 2 or 3.

The compounds of the formula (I) are preferably amorphous and have high glass transition temperatures.

Preference is given to compounds of the formula (I) in which a) $X^{1-4}$ are identical or b) $X^1$ is identical to $X^2$ and $X^3$ is identical to $X^4$.

Particular preference is given to the following compounds of the formula (I):

a)
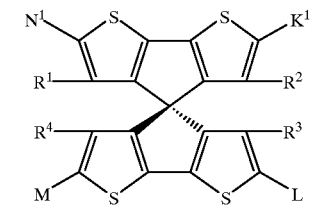

b)
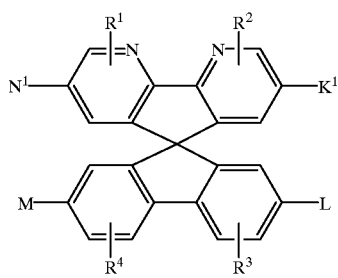

c)
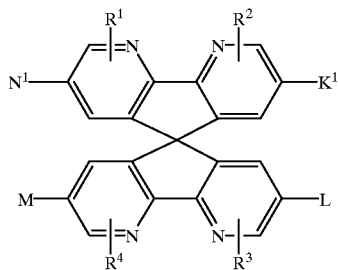

Very particular preference is given to spirofluorene derivatives of the formulae (I) a–c in which the symbols have the following meanings:

I.a) $K^1=L=M=N^1$ and is selected from the group consisting of:

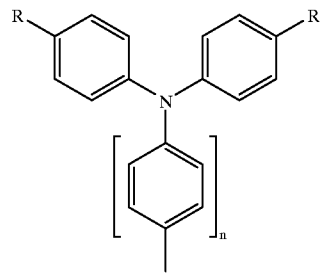

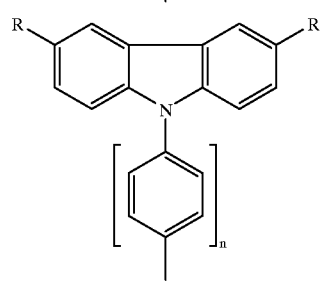

-continued

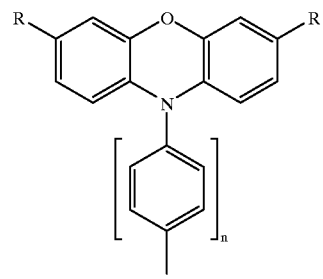

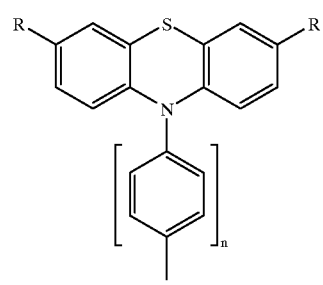

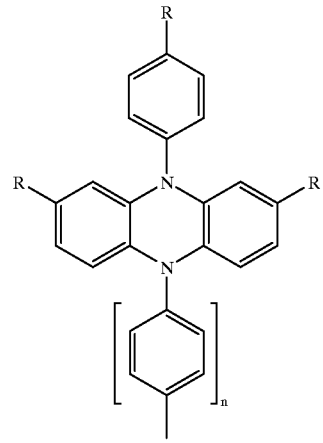

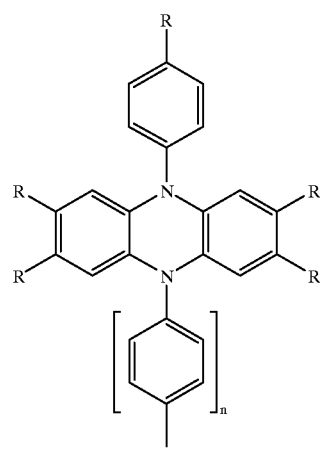

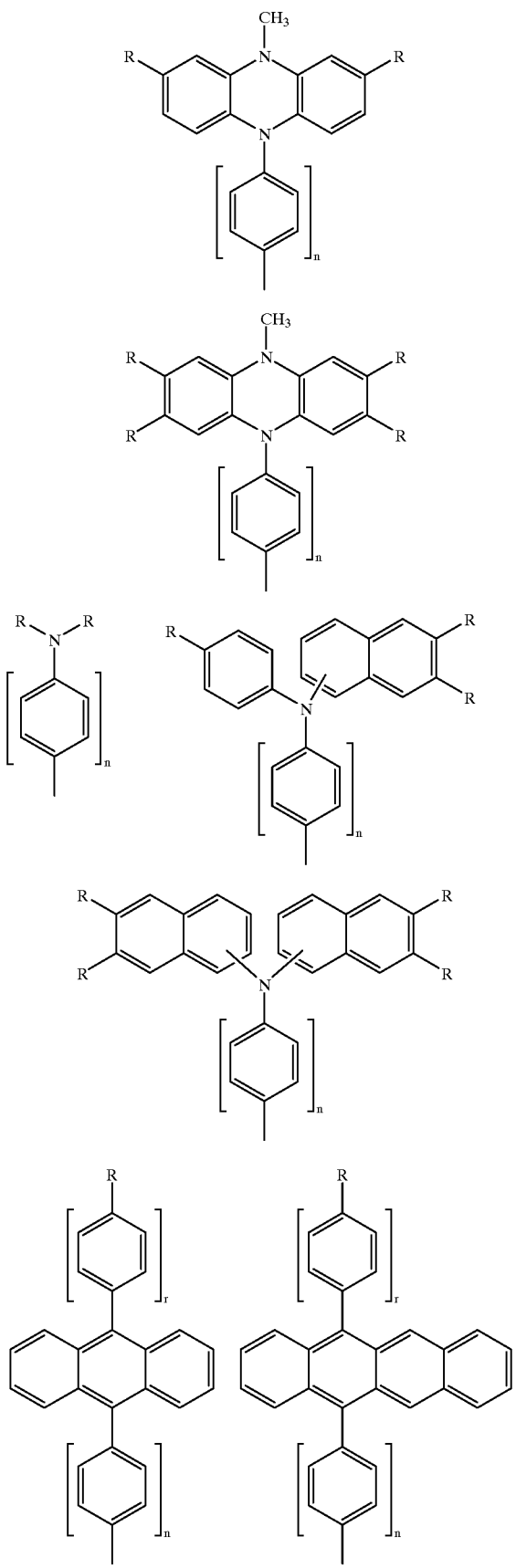
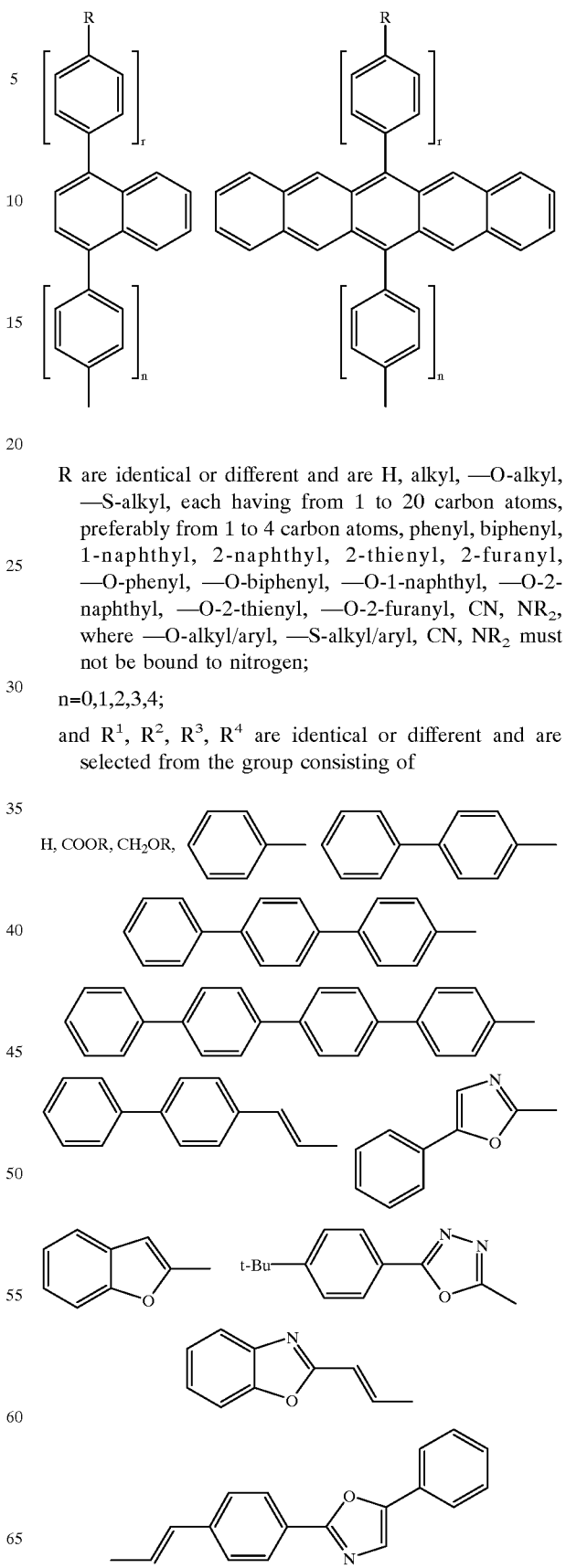

R are identical or different and are H, alkyl, —O-alkyl, —S-alkyl, each having from 1 to 20 carbon atoms, preferably from 1 to 4 carbon atoms, phenyl, biphenyl, 1-naphthyl, 2-naphthyl, 2-thienyl, 2-furanyl, —O-phenyl, —O-biphenyl, —O-1-naphthyl, —O-2-naphthyl, —O-2-thienyl, —O-2-furanyl, CN, $NR_2$, where —O-alkyl/aryl, —S-alkyl/aryl, CN, $NR_2$ must not be bound to nitrogen;

n=0,1,2,3,4;

and $R^1$, $R^2$, $R^3$, $R^4$ are identical or different and are selected from the group consisting of

H, COOR, $CH_2OR$,

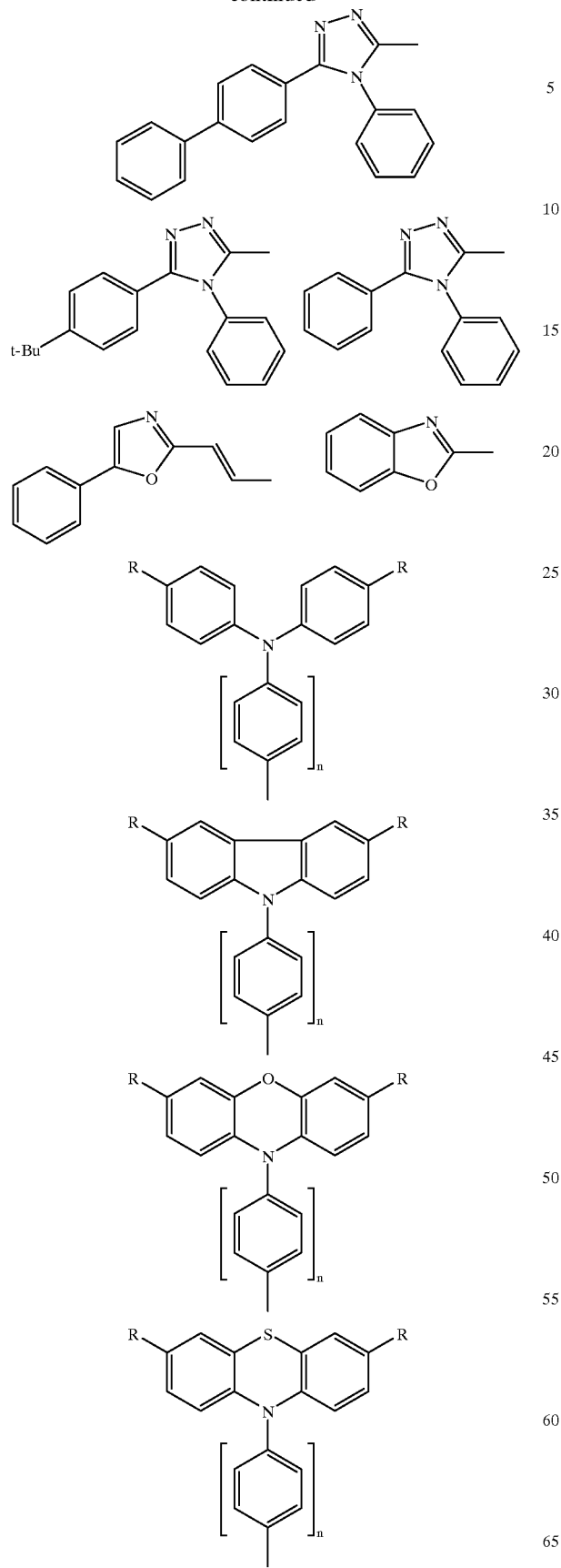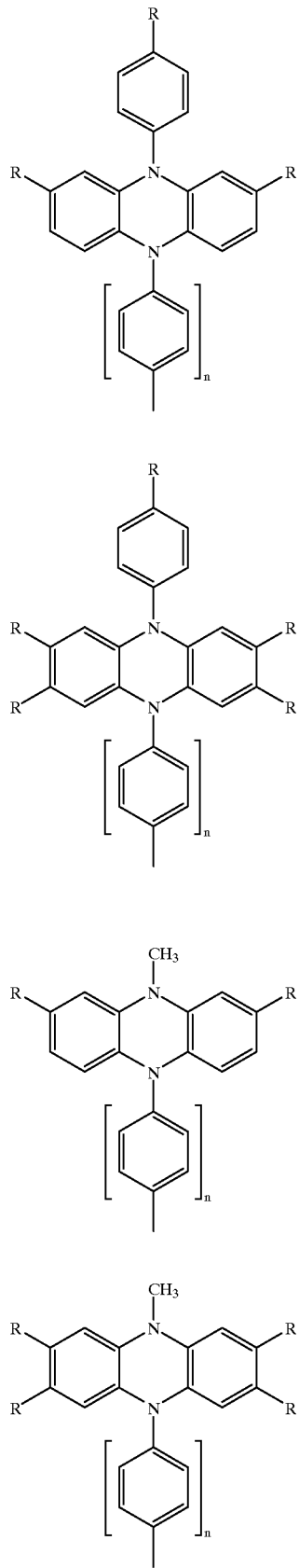

-continued
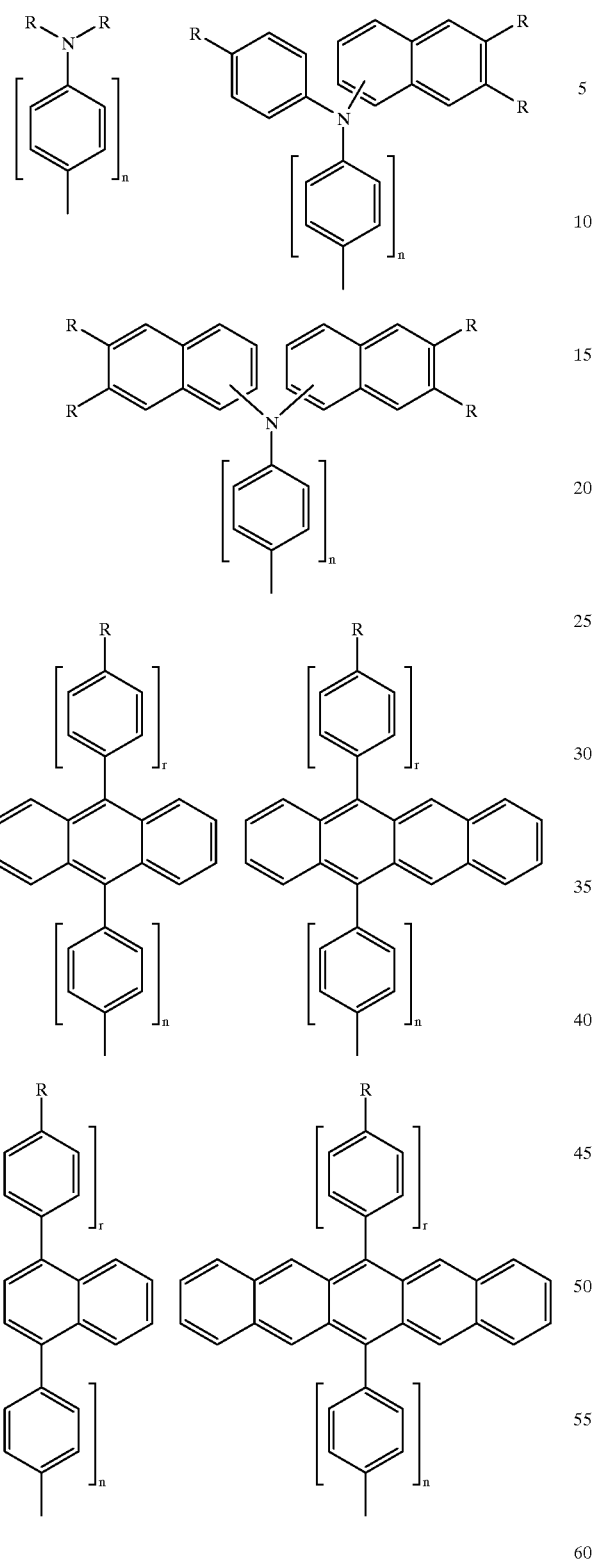
where the symbols and indices are as defined above and preferably at least two of the radicals $R^{1-4}$ are H;
I.b) $K^1 = N^1$ and is selected from the group consisting of
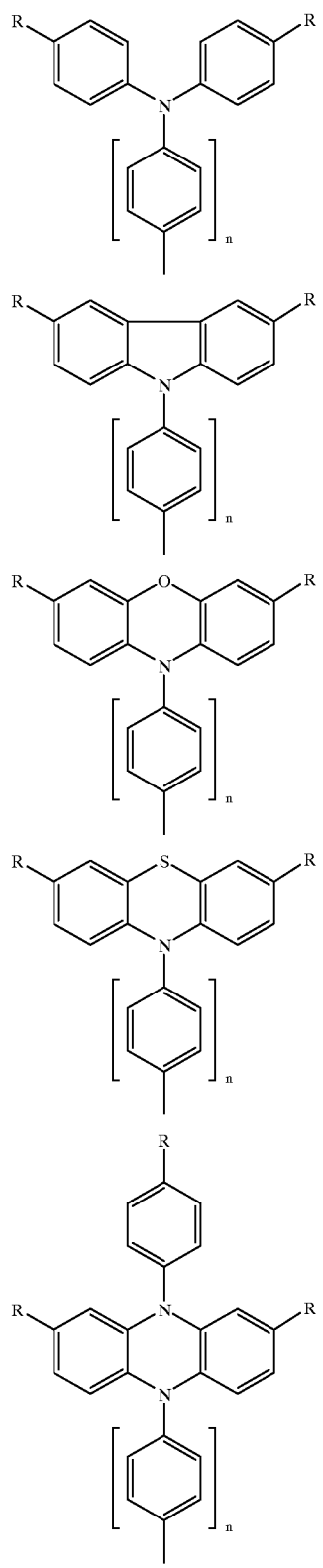

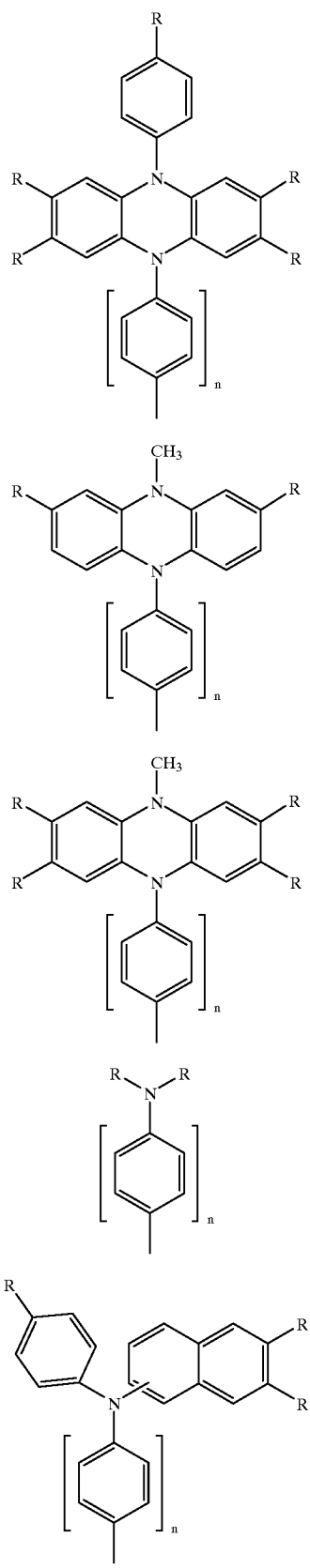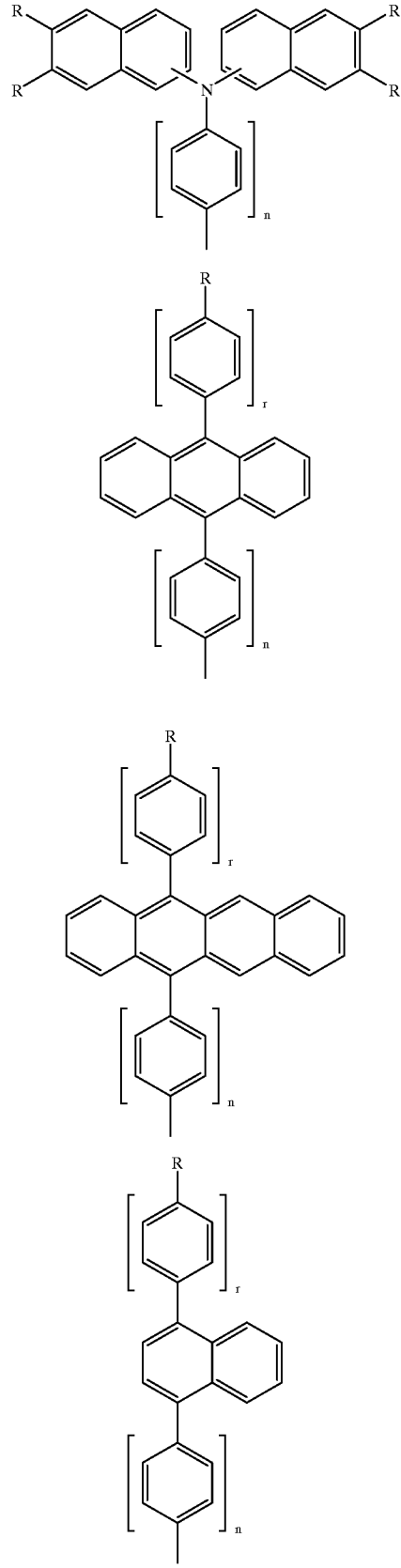

-continued
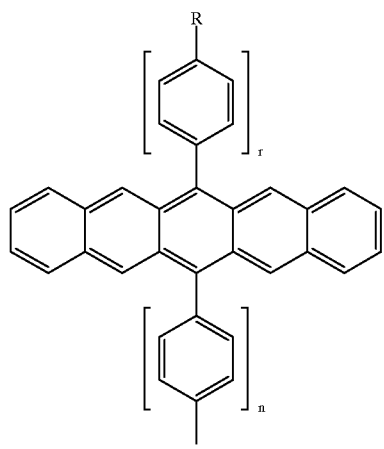
and L=M and is selected from the group consisting of
H, COOR, CH₂OR,
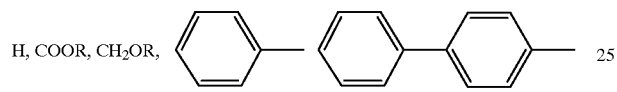
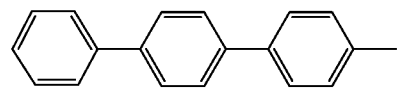
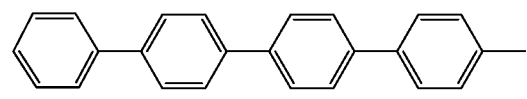
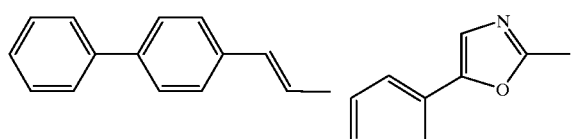
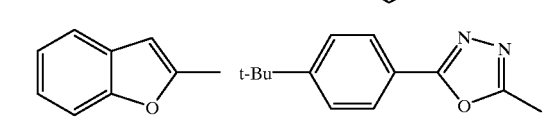
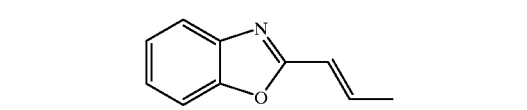
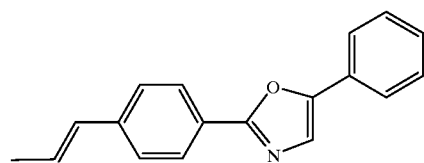
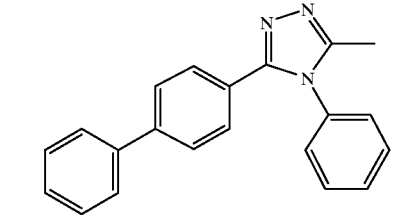
-continued
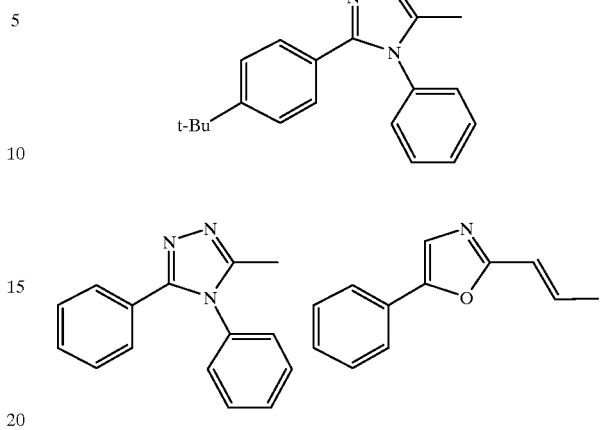
and R¹, R², R³, R⁴ are identical or different and are selected from the group consisting of
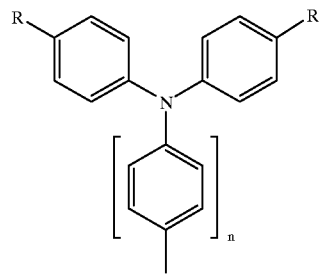
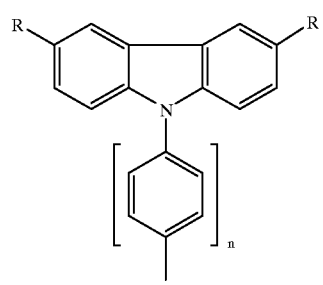
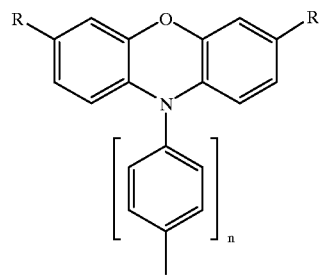

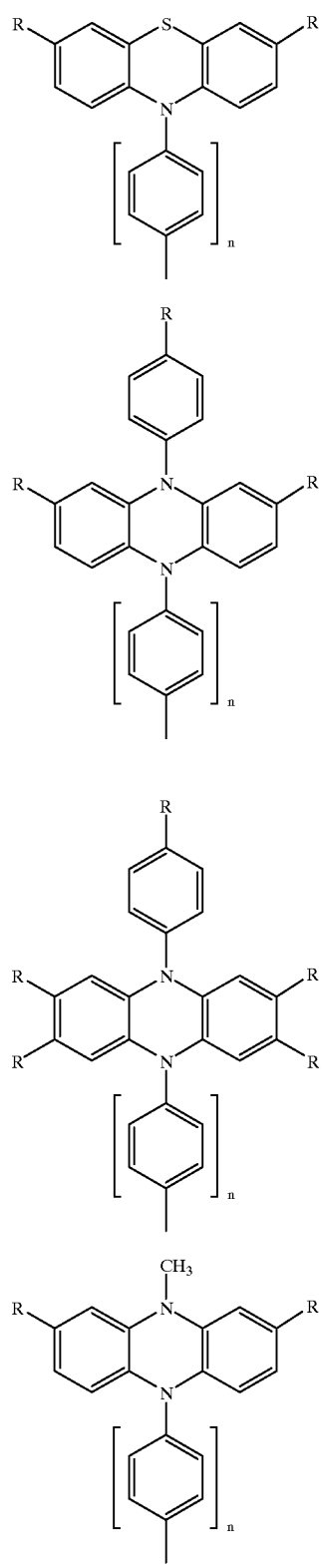
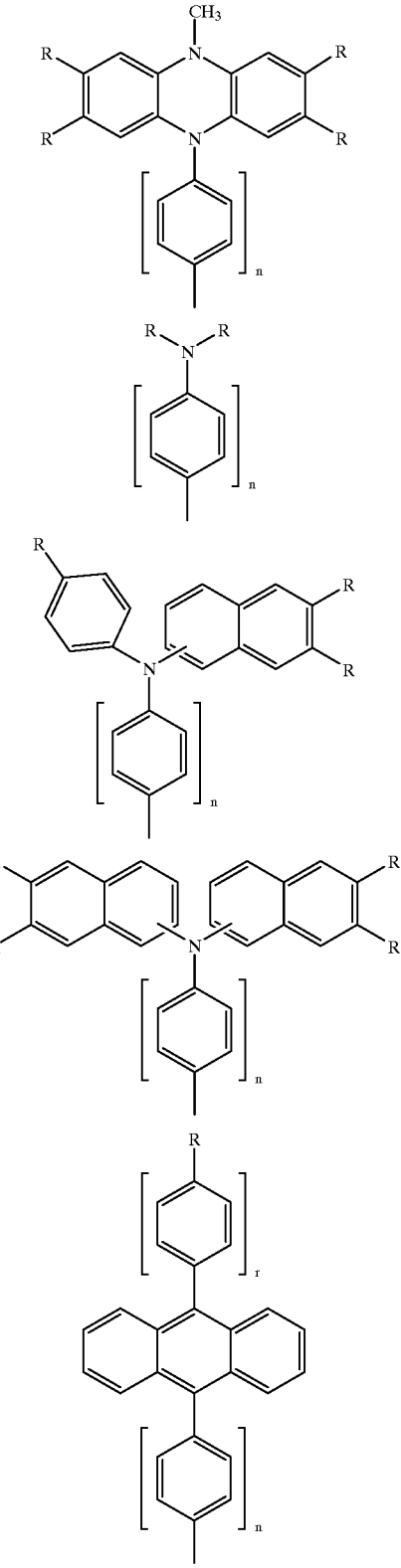

-continued
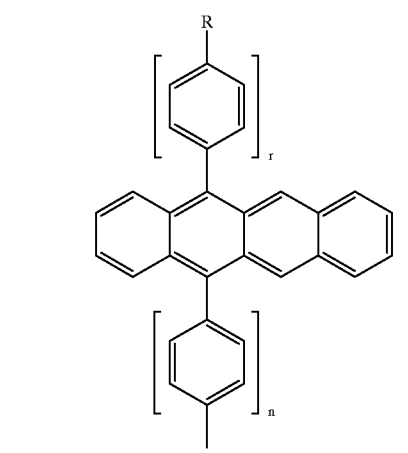
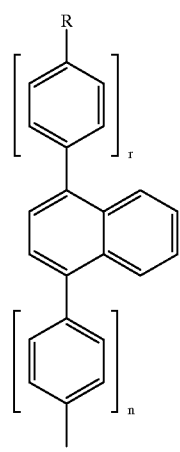
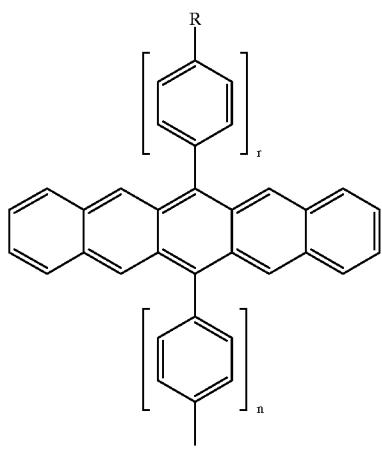
H, COOR, CH₂OR, 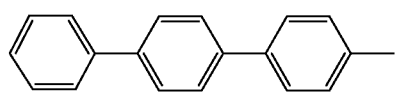
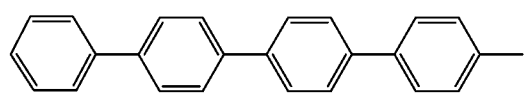
-continued
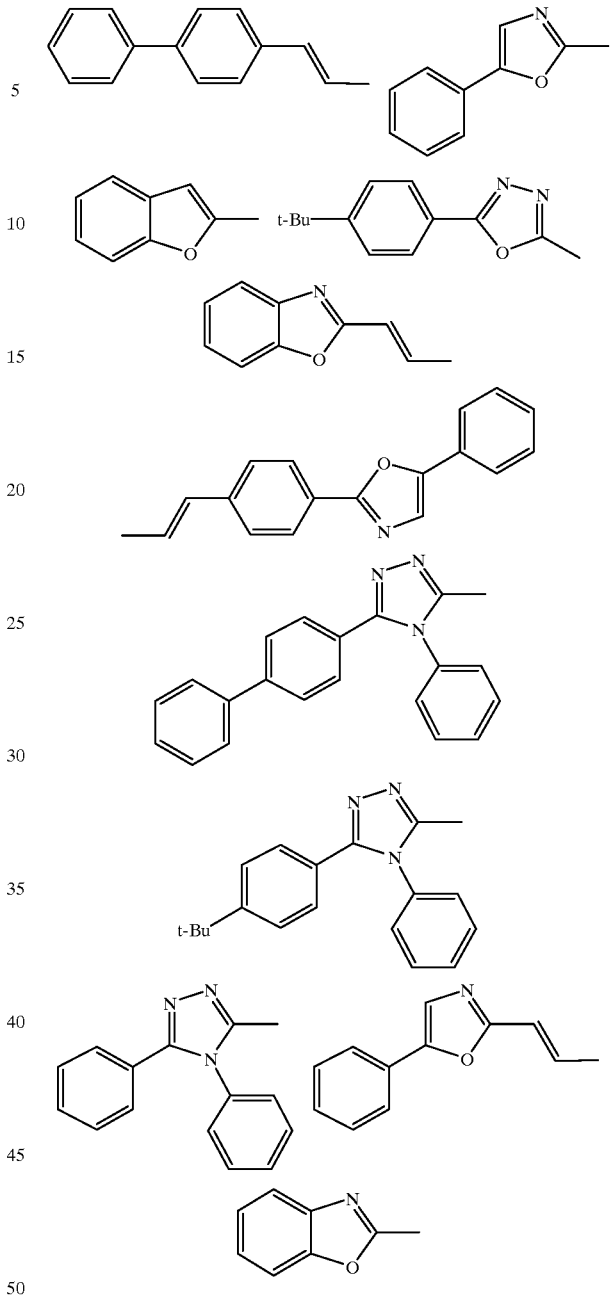
where the symbols and indices are as defined above and preferably at least two of the radicals $R^{1-4}$ are H;
Ic) $K^1$=M and is selected from the group consisting of
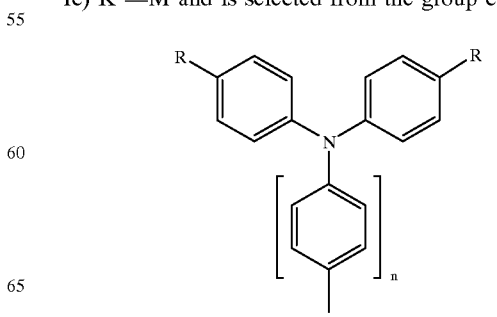

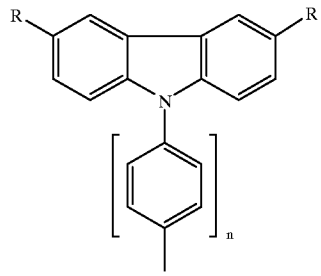
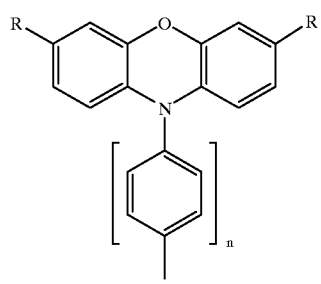
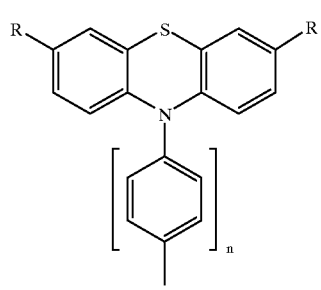
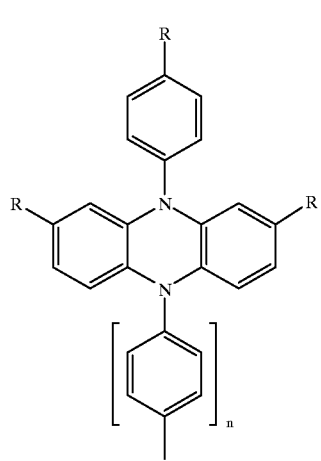
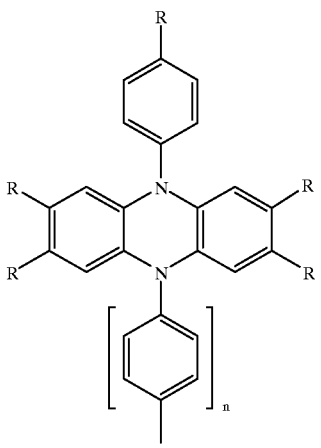
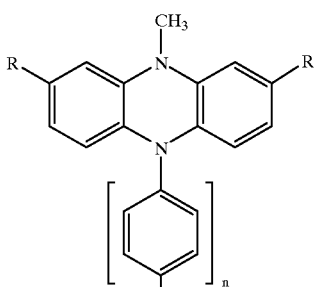
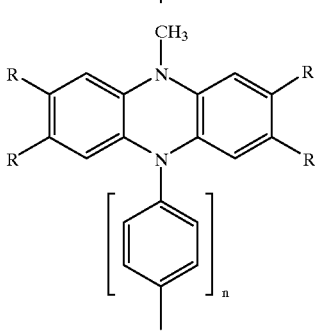
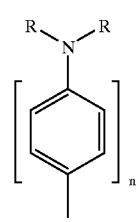
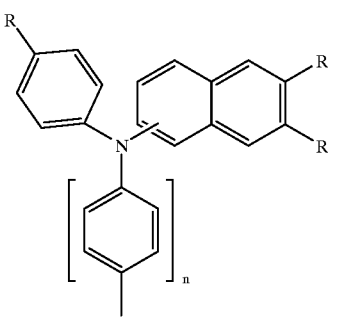

-continued
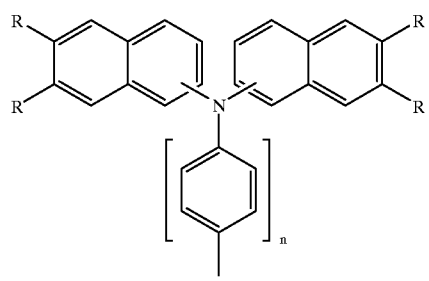
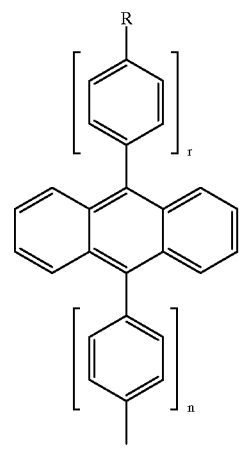
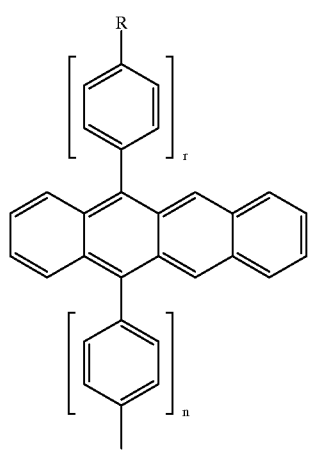
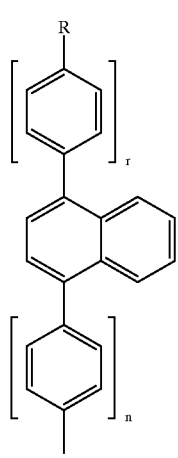
-continued
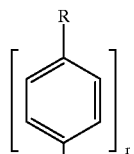
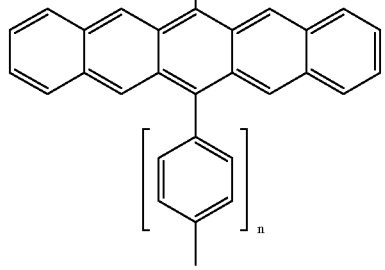
and M=N¹ and is selected from the group consisting of
H, COOR, CH₂OR, 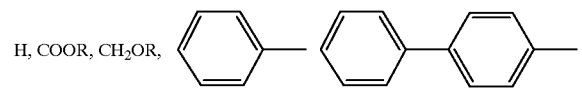
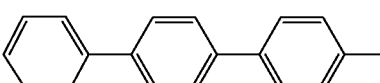
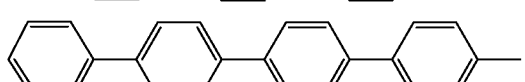
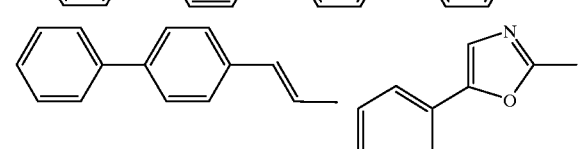
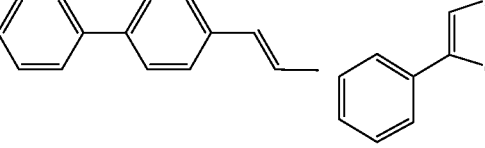
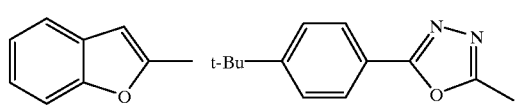
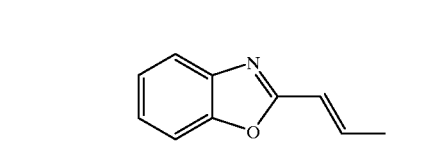
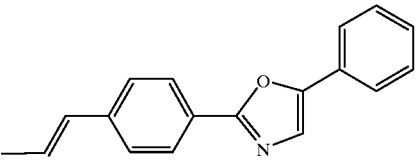
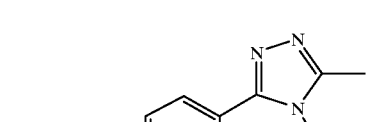
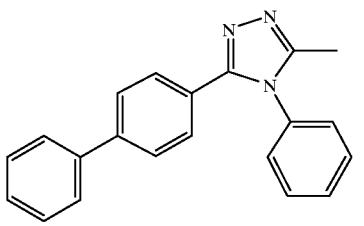
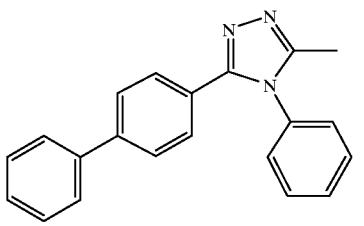

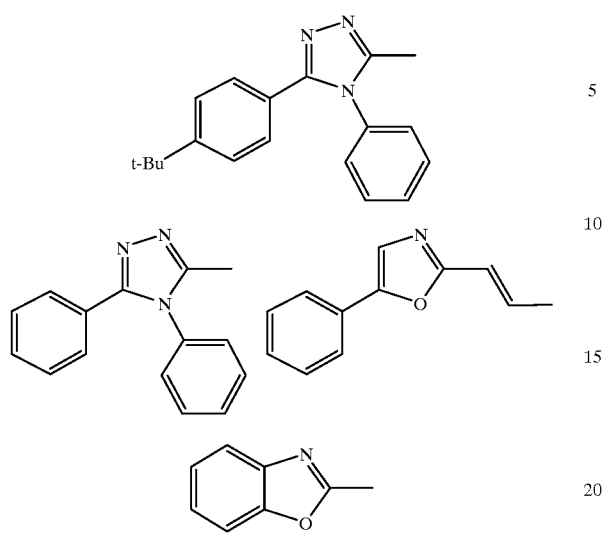
and $R^1$, $R^2$, $R^3$, $R^4$ are identical or different and are selected from the group consisting of
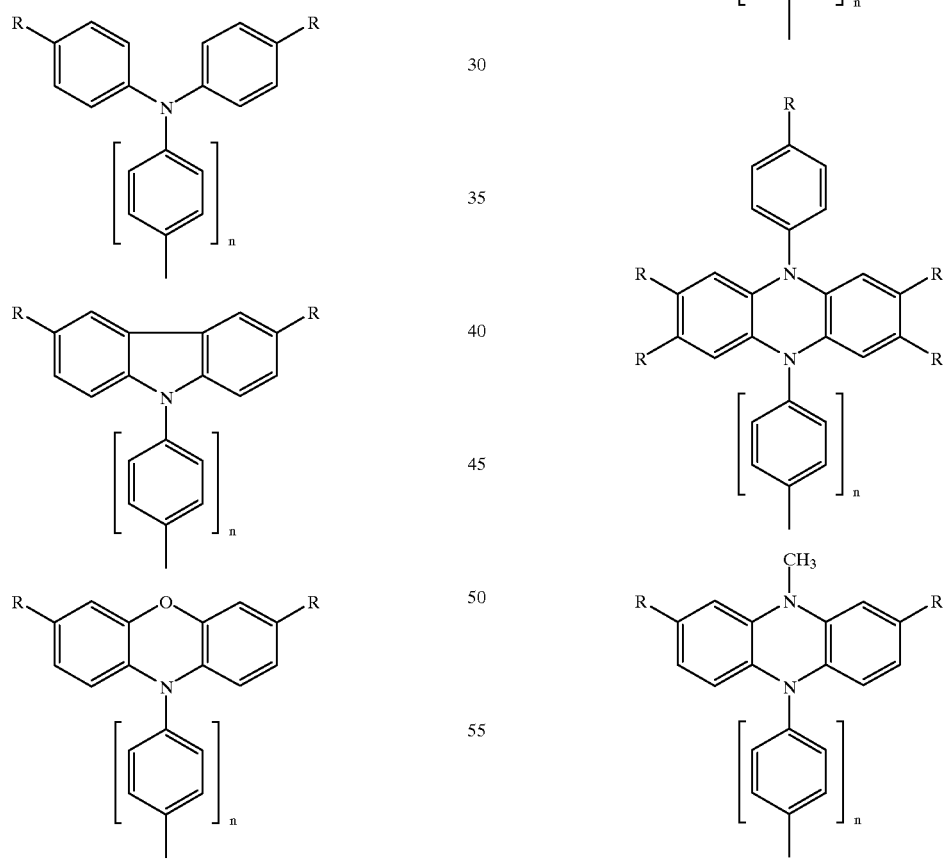

-continued
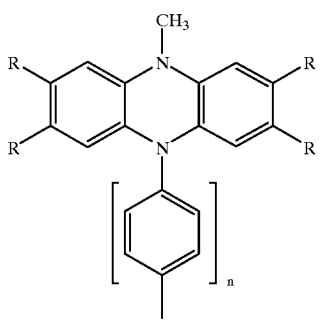
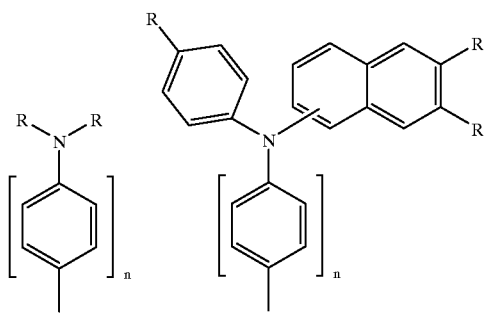
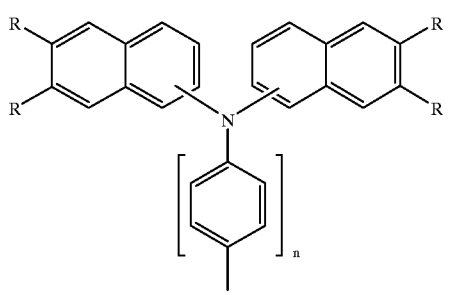
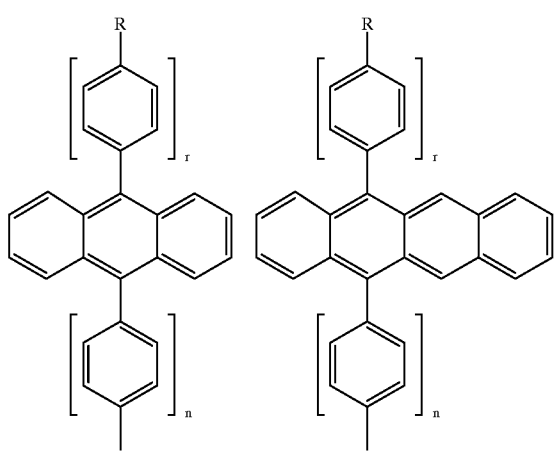
-continued
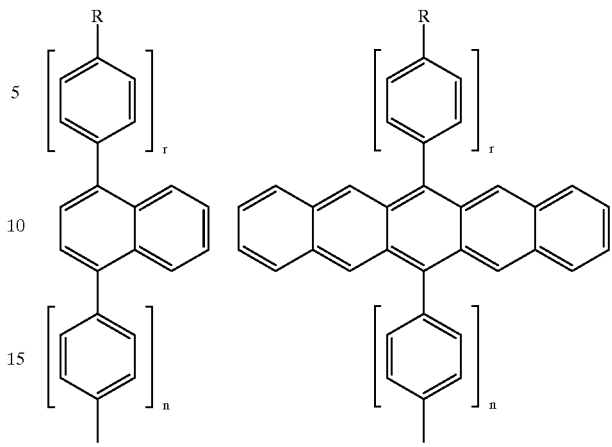
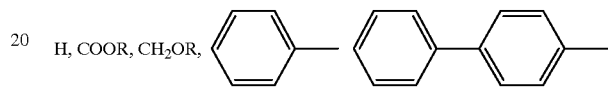
H, COOR, CH$_2$OR,
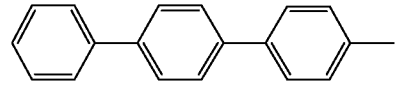
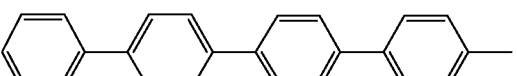
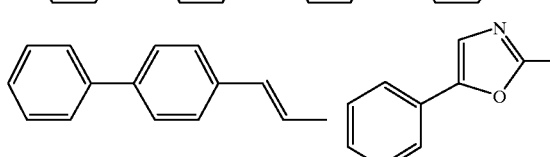
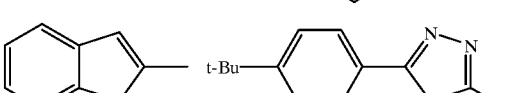
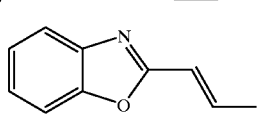
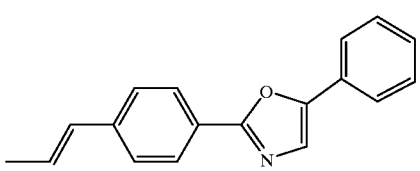
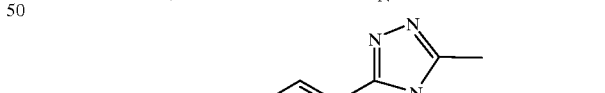
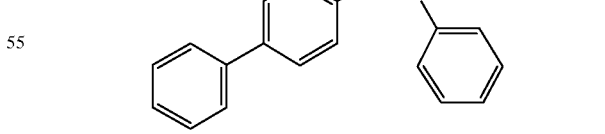
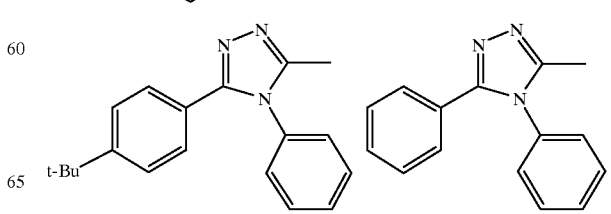

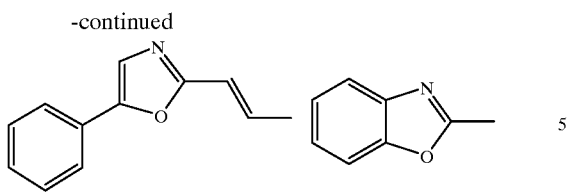
where the symbols and indices are as defined above and preferably at least two of the radicals $R^{1-4}$ are H.
Most preferred are the following compounds of the formula (I):
Iaa) $K^1=L=M=N^1$ and is selected from the group consisting of:
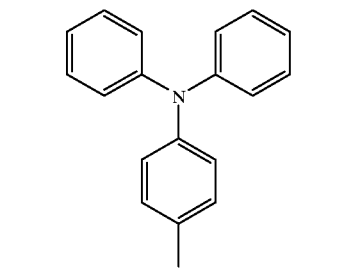
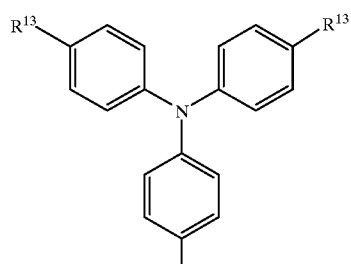
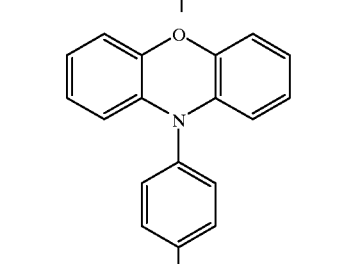
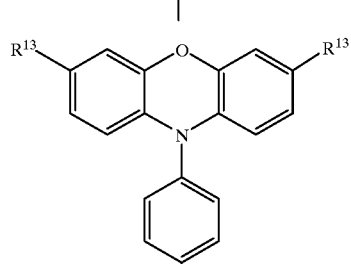
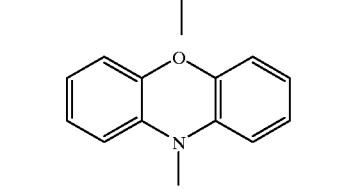
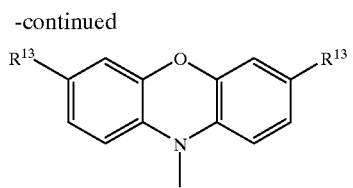
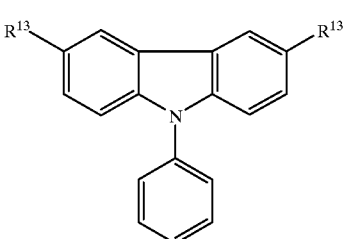
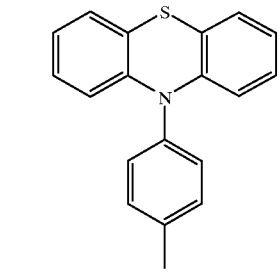
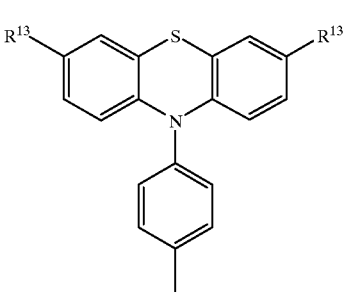
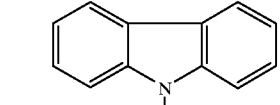
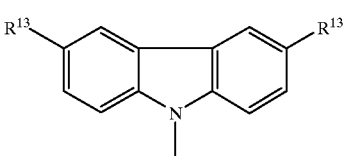

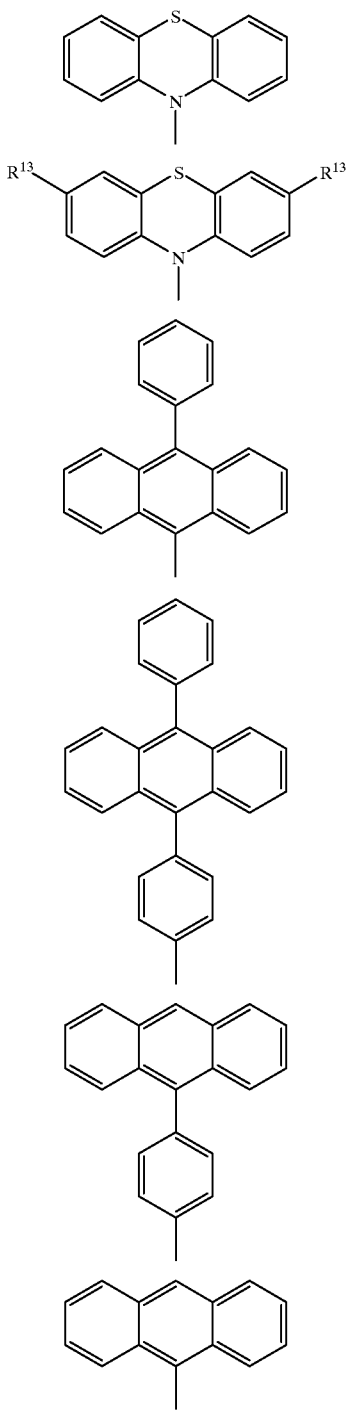

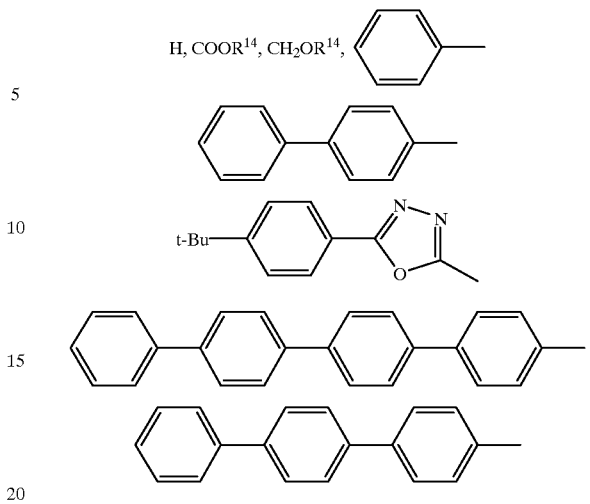

where $R^{14}$ is a straight-chain or branched alkyl group having from 1 to 12, preferably from 1 to 4 carbon atoms and preferably at least two of the radicals $R^{1-4}$ are H;

I.ba) $K^1$=L=M=$N^1$ and is selected from the group consisting of

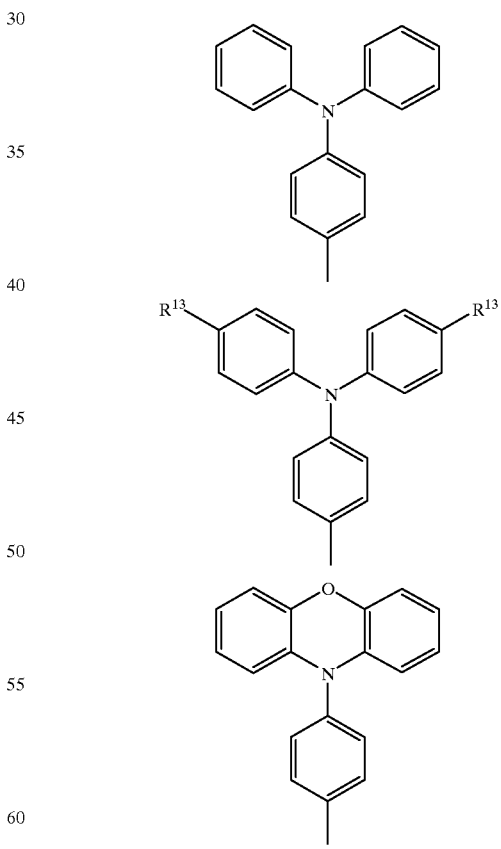

where $R^{13}$ is —O—CH$_3$, —O—C$_2$H$_5$, —S—CH$_3$, —S—C$_2$H$_5$, preferably —O—CH$_3$, —S—CH$_3$, particularly preferably —O—CH$_3$;

and $R^1$=$R^2$=$R^3$=$R^4$ and is selected from the group consisting of

-continued
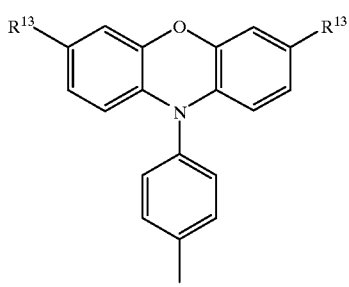
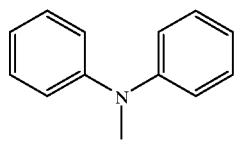
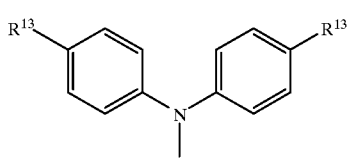
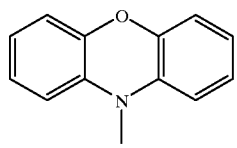
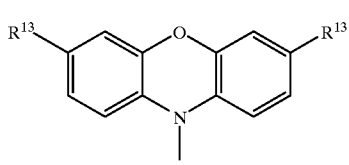
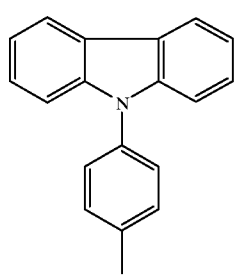
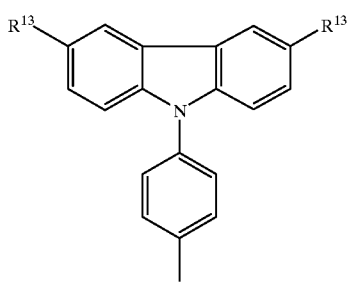
-continued
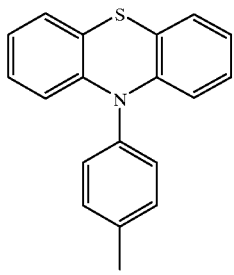
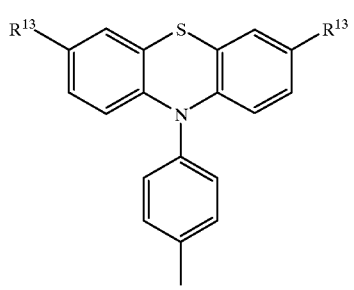
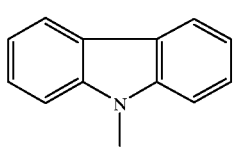
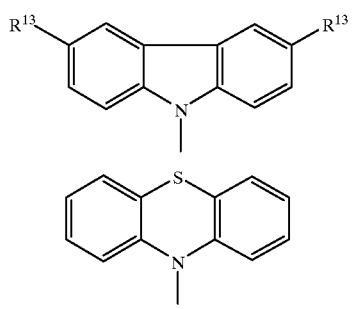
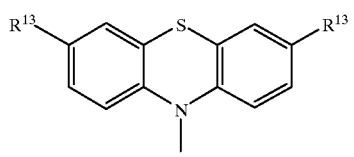
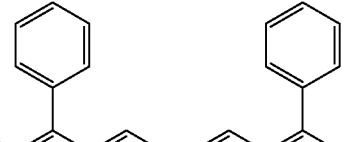
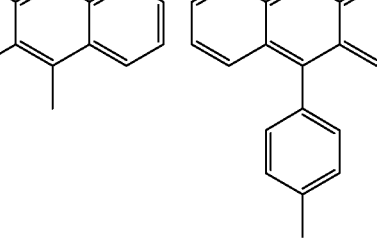

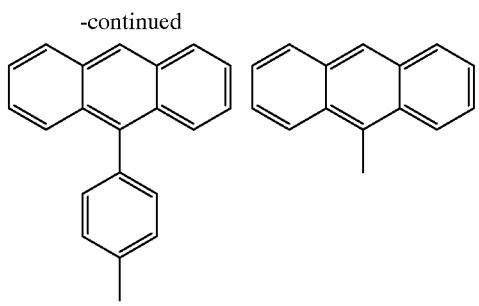
where R$^{13}$ is as defined above and R$^1$, R$^2$, R$^3$, R$^4$ are H;
I.ca) K$^1$=L=M=N$^1$ and is selected from the group consisting of
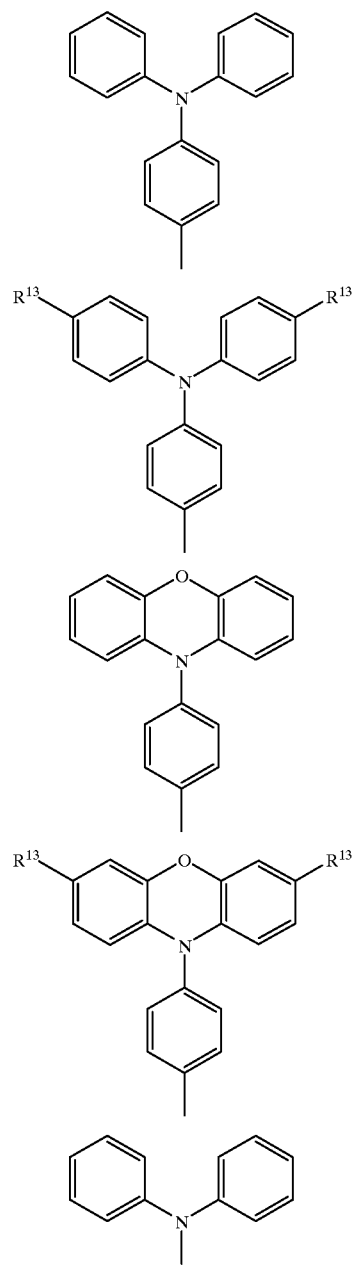
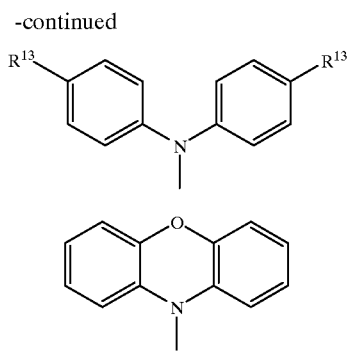
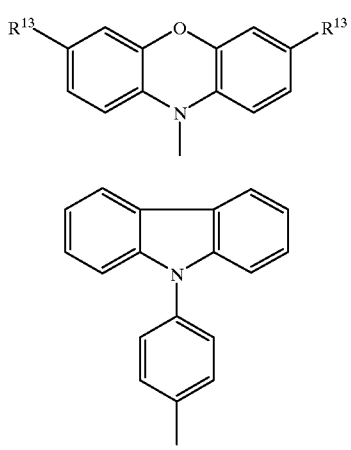

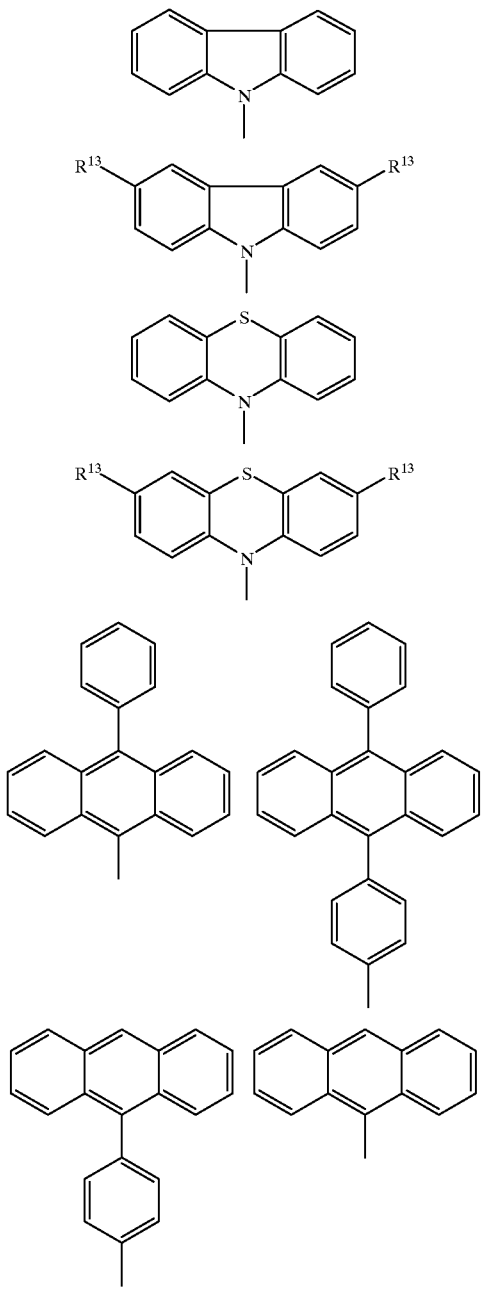

and three of the radicals $R^1$, $R^2$, $R^3$, $R^4$ are H and one is selected from the group consisting of

H, $COOR^{14}$, $CH_2OR^{14}$,

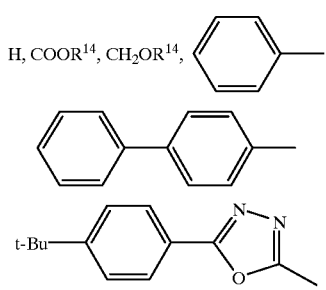

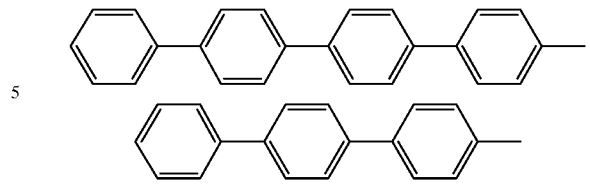

where $R^{13}$, $R^{14}$ are as defined above.

The spiro compounds of the invention are prepared by methods known per se from the literature, as are described in standard works on organic synthesis, e.g. Houben-Weyl, Methoden der Organischen Chemie, Georg-Thieme-Verlag, Stuttgart and in the appropriate volumes of the series "The Chemistry of Heterocyclic Compounds" by A. Weissberger and E. C. Taylor (editors).

The preparation is carried out under reaction conditions which are known and suitable for the reactions mentioned. It is also possible to make use of variants which are known per se but are not mentioned in more detail here.

The preparation of compounds of the formula (Ia) can, for example, be carried out starting with a tetrahalogenation of the basic spiro molecule and a subsequent substitution reaction (for example by a method similar to that described in U.S. Pat. No. 5,026,894) or can be carried out via a tetraacetylation with subsequent C-C linkage after conversion of the acetyl groups into aldehyde groups or heterocycle formation after conversion of the acetyl groups into carboxylic acid groups.

The preparation of compounds of the formula (Ib) can, for example, be carried out by methods similar to those for the formula (Ia), with the stoichiometric ratios in the reaction being selected so that the positions corresponding to the 2,2' or 7,7' positions of the spirofluorene are functionalized (see, for example, J. H. Weisburger, E. K. Weisburger, F. E. Ray, J. Am. Chem. Soc. 1959, 72 4253; F. K. Sutcliffe, H. M. Shahidi, D. Paterson, J. Soc. Dyers Colour 1978, 94, 306 and G. Haas, V. Prelog, Helv. Chim. Acta 1969, 52 1202).

The preparation of compounds of the formula (Ic) can, for example, be carried out via a dibromination in the appropriate position and subsequent diacetylation with subsequent reaction similar to that for the compounds (Ia).

Compounds of the formula (I) where $K^1$, L, $R^1$, $R^2$, $R^3$, $R^4$=H and M=$N^1$ or $R^1$, $R^2$, $R^3$, $R^4$ =H, $K^1$=L and M=$N^1$ can be prepared, for example, by choice of appropriately substituted starting compounds in building up the spiro framework.

For the synthesis of the groups $K^1$, L, M, $N^1$, $R^1$, $R^2$, $R^3$, $R^4$, reference may be made, for example, to DE-A 23 44 732, which is equivalent to U.S. Pat. No. 3,826,727, DE-A 24 50 088, which is equivalent to U.S. Pat. Nos. 4,065,489 and 4,136,053, DE-A 24 29 093, 25 02 904, 26 36 684, 27 01 591 and 27 52 975 for compounds having 1,4-phenylene groups; DE-A 26 41 724 for compounds having pyrimidine-2,5-diyl groups; DE-A 40 26 223 and EP-A 03 91 203 for compounds having pyridine-2,5-diyl groups; DE-A 32 31 462 for compounds having pyridazine-3,6-diyl groups; N. Miyaura, T. Yanagi and A. Suzuki in Synthetic Communications 1981, 11, 513 to 519, DE-A-39 30 663; M. J. Sharp, W. Cheng, V. Snieckus, Tetrahedron Letters 1987, 28, 5093; G. W. Gray, J. Chem. Soc. Perkin Trans II 1989, 2041 and Mol. Cryst. Liq. Cryst. 1989, 172,165; Mol. Cryst. Liq. Cryst. 1991, 204, 43 and 91; EP-A 0 449 015; WO 89/12039; which is equivalent to U.S. Pat. No. 5,182,047, WO 89/03821; EP-A 0 354 434 for the direct coupling of aromatics and heteroaromatics.

The preparation of disubstituted pyridines, disubstituted pyrazines, disubstituted pyrimidines and disubstituted pyridazines is described, for example, in the appropriate volumes of the series "The Chemistry of Heterocyclic Compounds" by A. Weissberger and E. C. Taylor (editors).

Amino compounds of the formula (I) can be built up via variants of the Ullmann reaction (J. March, Adv. Org. Chem., 4th edition, p. 665, John Wiley & Sons, New York 1992), as is described, for example, in Chem. Lett. 1989, 1145; Mol. Cryst. Liq. Cryst. 1994, 242, 127 and particularly in J. Salbeck et al., 213th ACS National Meeting, San Francisco 1997, Book of Abstracts, p. 199.

A further possibility is a process known from U.S. Pat. No. 5,576,460. Preference is given to preparing such compounds by a process disclosed in the German patent application 197 38 860.4 having the title "Verfahren zur Herstellung von Acyloligoaminen". This application is expressly incorporated by reference into the present description.

The novel Spiro compounds of the formula (I) are suitable as charge transport materials, preferably for photovoltaic cells.

The invention therefore also provides for the use of spiro compounds of the formula (I) as charge transport material, in particular for photovoltaic cells.

The invention further provides a photovoltaic cell having a charge transport layer comprising, preferably consisting of, one or more, preferably one, spiro compound(s) of the formula (I).

FIG. 1 shows a preferred embodiment of such a cell 1 (not to scale). A conductive support 11, which can serve as electrode or contact and comprises, for example, a metal or indium-tin oxide (ITO), has applied to it a semiconductor 12 which serves as light-absorbing layer and preferably has a surface having a roughness factor of >1. The cell of the invention preferably has a chromophore, here shown as chromophore layer 13, on the surface of the semiconductor. For the purposes of the present invention, the term light-absorbing layer encompasses both a semiconductor layer and a combination of semiconductor/chromophore, even if it is the chromophore which is almost entirely responsible for the actual absorption in this case. This is adjoined by the charge transport layer 14 which according to the invention comprises a spiro compound of the formula (I). It is bounded on one side by the counterelectrode 15 which can comprise, for example, a conductive glass, conductively coated plastic, metal or another conductive, preferably translucent, material. The cell 1 is preferably closed off at the top and bottom by insulating layers 16 and 17. It can also have a lateral closure not shown in the figure, for example a frame of electrically insulating material such as plastic or glass. However, the use of a hole conductor material in place of the liquid electrolyte makes such a lateral frame unnecessary in principle. At least one side of the cell must be translucent so that the light to be converted into electric energy can reach the chromophore or the semiconductor. In addition, the cell comprises devices not shown in the figure for taking off the electric current generated by the cell.

The photovoltaic cell of the invention preferably comprises, as light-absorbing layer, a semiconductor which preferably has a very large band gap, particularly preferably at least 3.0 eV, very particularly preferably above 3.0 eV.

As semiconductors, preference is given to metal oxide semiconductors, particularly the oxides of the transition metals and also of the elements of main group III and of transition groups IV, V and VI (of the Periodic Table of the Elements), of titanium, zirconium, hafnium, strontium, zinc, indium, yttrium, lanthanum, vanadium, niobium, tantalum, chromium, molybdenum, tungsten, but also oxides of zinc, iron, nickel or silver, perovskites such as $SrTiO_3$, $CaTiO_3$, or oxides of other metals of main groups II and III or mixed oxides or oxide mixtures of these metals. However, it is also possible to use any other metal oxide having semiconducting properties and a large energy difference (band gap) between valence band and conduction band.

Titanium dioxide is particularly preferred as semiconductor material.

The semiconductor preferably has a roughness factor of greater than 1, particularly preferably greater than 20, very particularly preferably greater than 150. The roughness factor is defined as the ratio of an actual/effective surface area to the area of projection of this surface of a body, in this case the surface of the semiconductor.

The roughness factor can be determined, for example, by gravimetric adsorption methods, as described, for example, in, F. Kohlrausch, Praktische Physik, Volume 1, p. 397 (Stuttgart: B. G. Teubner, 1985). In general, the size of the pores is 5–200 nm, preferably 10–50 nm.

A method of preparing polycrystalline metal oxide semiconductor layers using the sol-gel process (described in detail in, for example, Stalder and Augustynski, J. Electrochem. Soc. 1979, 126, 2007), where, in the process step of hydrolysis of the metal alkoxide, the percentage relative humidity of the surrounding atmosphere can be in a range from 30% to 80% and is kept constant within ±5%, preferably ±1%, gives metal oxide semiconductor layers by means of which a particularly high electric yield can be achieved in photovoltaic cells according to the invention. The rough surface having a polycrystalline structure provides an area increased by the roughness factor for a preferably monomolecular surface layer of a chromophore. As a result, the light incident on an area of particular size is converted into electric energy in significantly higher yield. The semiconductor can be regarded as transparent to the incident light. However, light is partially reflected on the surface and some of it reaches adjacent surfaces. The light which penetrates into the semiconductor and is not absorbed or converted reaches, partly directly and partly indirectly and also partly indirectly after total reflection on the surface, chromophore molecules on the exit side, as a result of which a significantly higher light yield can be achieved.

The sensitivity, i.e. the photoelectronic yield for visible light, thus also for sunlight, can therefore be increased by chromophores, also known as sensitizers or dyes, as charge carriers being chemically bound on or in (chemisorbed) the surface of the semiconductor. The two functions of light absorption and charge carrier separation are separated in these photoelectronic systems. The light absorption is performed by the chromophore in the surface region and the separation of the charge carriers occurs at the semiconductor/chromophore interface. Various chromophores have different spectral sensitivities. The choice of chromophore can thus be matched to the spectral composition of the light from the light source in order to increase in the yield as much as possible. Suitable chromophores, i.e. sensitizers, are, in particular, the complexes of transition metals of the type metal($L_3$), metal($L_2$) of ruthenium and osmium (e.g. ruthenium-tris(2,2-bipyridyl-4,4'-dicarboxylic acid)) and their salts, ruthenium cis diaqua bipyridyl complexes such as ruthenium cis-diaqua-bis(2,2'-bipyridyl-4,4'-dicarboxylates) and also porphyrins (e.g. zinc tetra(4-carboxyphenyl)porphyrin) and cyanides (e.g. iron-hexacyanide complexes) and phthalocyanines. The chromophores can be chemisorbed, adsorbed or otherwise fixed in the region of the surface of the metal oxide semiconductor. Good results were obtained, for example, using chromophores which are bound via carboxylic acid or phosphonic acid ligands to the surface of the metal oxide semiconductor.

Suitable chromophores are described, for example, in Chem. Rev. 1995, 49–68.

Particular preference is given to ruthenium-tris(2,2'-bipyridyl-4,4'-dicarboxylic acid), its salts and the chromophores (VIII) and (IX), (VIII)

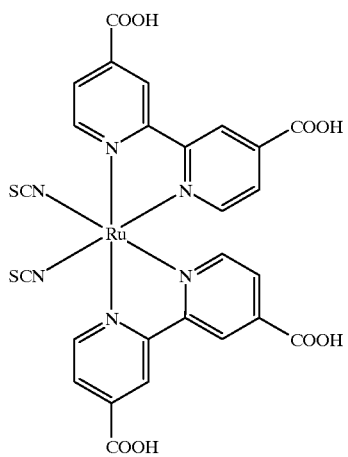

(IX)

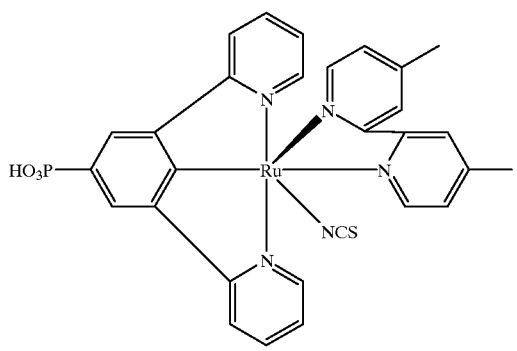

whose synthesis and properties are described in J. Chem. Soc. Chem. Comm. 1995, 65.

The application of the chromophore, for example ruthenium-tris(2,2'-bipyridyl-4,4'-dicarboxylic acid) or a salt thereof, is carried out, for example, by dipping the substrate with the oxide layer into a solution, for example an aqueous or alcoholic, preferably ethanolic, solution for about one hour. The concentration of the solution is preferably from 0.1 to 10 molar, particularly preferably from 1 to 5 molar, for example 2 molar. Other chromophores can be applied to titanium oxide or other metal oxide semiconductors by analogous methods.

Materials suitable as electrode 15 are stable, metallically conductive substances, e.g. Au, Ag, Pt, Cu or other metals. However, for some applications it is possible to use preferably translucent conductive substances such as doped metal oxides, e.g. indium-tin oxide, Sb-doped tin oxide or Al-doped zinc oxide. The work function of the electrode material used is preferably matched to the ionization potential of the hole transport material employed.

The electrode can, as described in EP-A 0 333 641, be applied to a transparent substrate, e.g. glass, and be joined to the hole transport layer. In the cell of the invention, it can advantageously be applied directly to the hole transport layer by physical deposition methods, e.g. vapor deposition or sputtering, without a second glass plate being necessary. This method is preferred in applications in which the weight of the cell is to be reduced.

If desired, the cell can be sealed, for example by means of an adhesive or a film.

A photovoltaic cell according to the invention generally has a thickness of from 5 to 20 mm (including substrate).

To avoid reflection losses, it can be provided with a single-layer, two-layer or multilayer antireflection coating.

Spiro compounds of the formula (I) are also suitable as electroluminescence materials.

For the purposes of the present invention, electroluminescence materials are materials which can be used as active layer in an electroluminescence device. Active layer means that the layer is capable of emitting light on application of an electric field (light-emitting layer) and/or that it improves the injection and/or transport of the positive and/or negative charges (charge injection layer or charge transport layer).

The invention therefore also provides for the use of a spiro compound of the formula (I) as electroluminescence material, i.e. as active layer in an electroluminescence device.

To be used as electroluminescence materials, the spiro compounds of the formula (I) are applied in the form of a film to a substrate, generally by known methods with which those skilled in the art are familiar, e.g. dipping or spin coating.

The invention further provides an electroluminescence device having one or more active layers of which at least one comprises one or more novel spiro compounds of the formula (I). The active layer can be, for example, a light-emitting layer and/or a transport layer and/or a charge injection layer.

The general structure of such electroluminescence devices is described, for example, in U.S. Pat. Nos. 4,539,507 and 5,151,629. Polymer-containing electroluminescence devices are described, for example, in WO-A 90/13148 or EP-A 0 443 861.

They customarily comprise an electroluminescence layer between a cathode and an anode, with at least one of the electrodes being transparent. In addition, one or more electron injection and/or electron transport layers can be inserted between the electroluminescence layer and the cathode and/or one or more hole injection and/or hole transport layers can be inserted between the electroluminescence layer and the anode. Materials employed as cathode are preferably metals or metallic alloys, e.g. Ca, Mg, Al, In, Mg/Ag. Materials employed as anode are metals, e.g. Au, or other metallically conductive materials such as oxides, e.g. ITO (indium oxide/tin oxide), on a transparent substrate, e.g. of glass or a transparent polymer.

In operation, the cathode is placed at a negative potential relative to the anode. As a result, electrons from the cathode are injected into the electron injection layer/electron transport layer or directly into the light-emitting layer. At the same time, holes from the anode are injected into the hole injection layer/hole transport layer or directly into the light-emitting layer.

The injected charge carriers move toward one another through the active layers under the action of the applied potential. This leads to electron-hole pairs at the interface between charge transport layer and light emitting layer or within the light-emitting layer and these pairs recombine with emission of light.

The color of the light emitted can be varied by means of the materials used as light-emitting layers.

Electroluminescence devices are employed, for example, as self-illuminating display elements such as indicator lamps, alphanumeric displays, signs, and in optoelectronic couplers.

The contents of the German patent application 197 11 568.3 having the title "Spiroverbindungen und deren Verwendung" on which the priority of the present application is based and also the contents of the abstract of the present application are hereby expressly incorporated by reference into the present application.

What is claimed is:

1. A spiro compound of the formula (I),

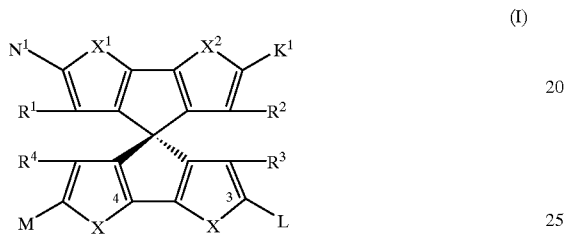
(I)

where the symbols have the following meanings:

$X^1$, $X^2$, $X^3$, $X^4$ are identical or different and are —S—, —O—, —NR$^5$—, —CR$^5$=N—, —CR$^5$=CH—,
with the proviso that at least one of the groups $X^{1-4}$ is different from —CR$^5$=CH—;

$K^1$, L, M, $N^1$, $R^1$, $R^2$, $R^3$, $R^4$ are identical or different and are each a) hydrogen, —NO$_2$, —CN, —F or —Cl, b) a straight-chain or branched alkyl radical having from 1 to 20 carbon atoms, where
  b1) one or more nonadjacent CH$_2$ groups can be replaced by —O—, —S—, —CO—O—, —O—CO—, —O—CO—O—, NR$^5$ or —Si(CH$_3$)$_2$— and/or
  b2) one or more CH$_2$ groups can be replaced by —CH=CH—, —C≡C—, 1,4-phenylene, 1,4-cyclohexylene or 1,3-cyclopentylene and/or
  b3) one or more H atoms can be replaced by F and/or Cl and/or c) one of the following groups:

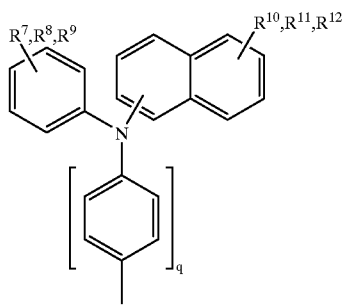

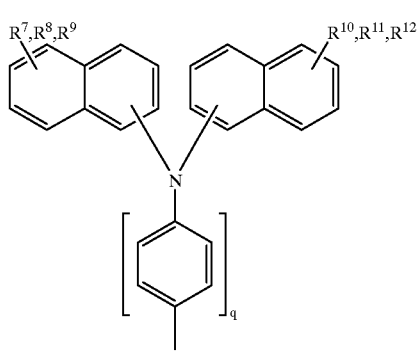

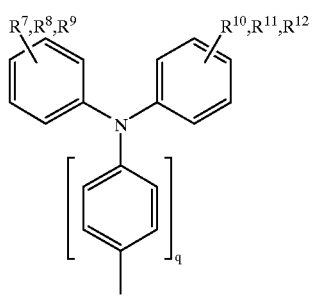

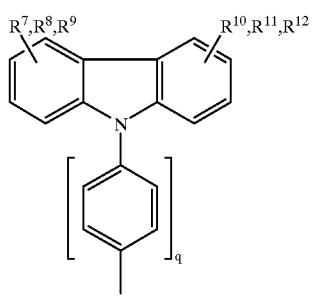

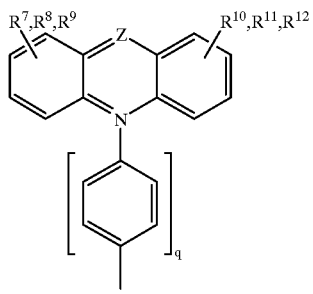
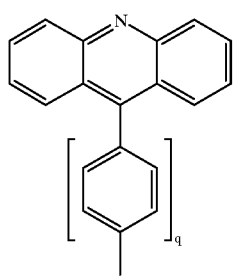
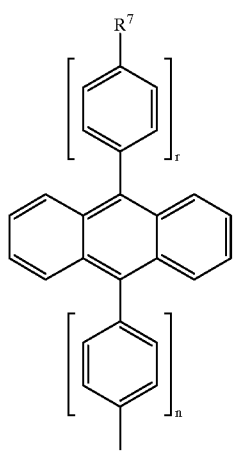
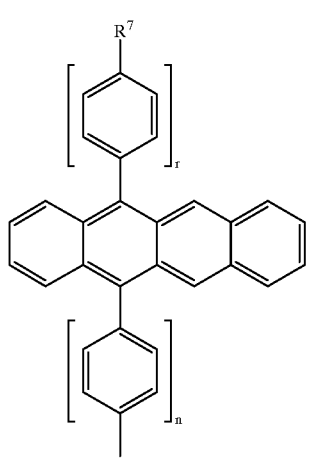
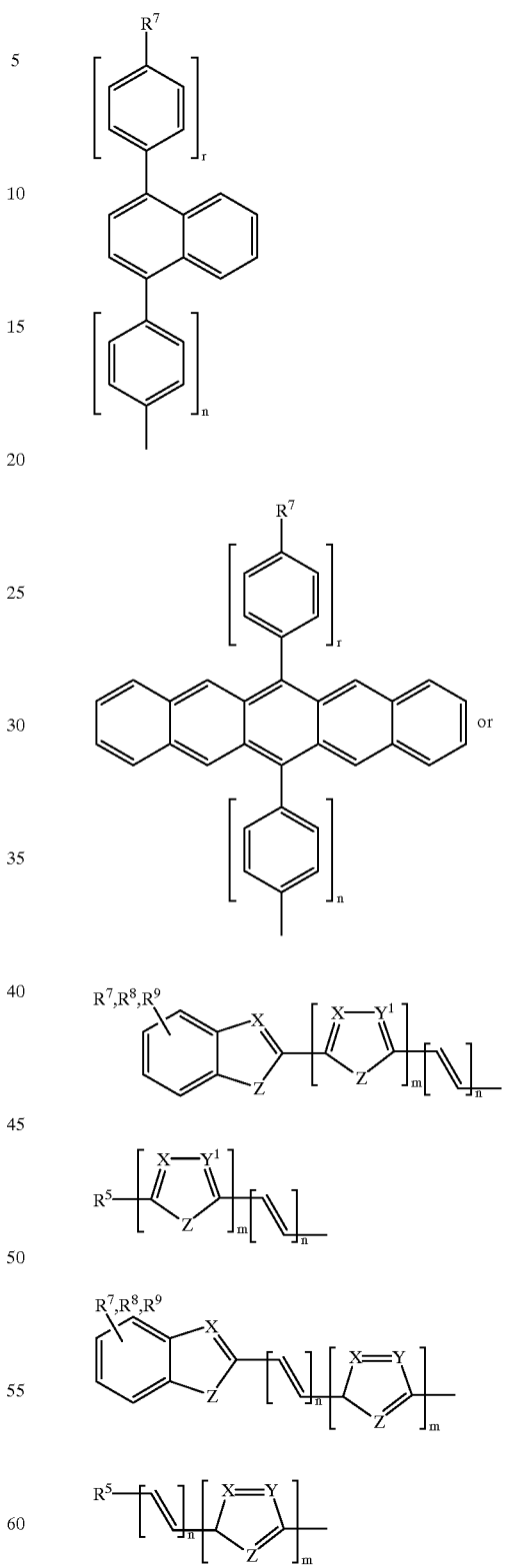
X, Y$^1$ are in each case identical or different and are =CR$^7$— or =N—;
Z is —O—, —S—, —NR$^5$—, —CRR—, —CR=CR— or —CR=N—;

$R^5$, $R^6$ are in each case identical or different and are each
- a) hydrogen
- b) a straight-chain or branched alkyl radical having from 1 to 20 carbon atoms, where
  - b1) one or more nonadjacent $CH_2$ groups which are not bound to nitrogen can be replaced by —O—, —S—, —CO—O—, —O—CO—, —O—CO—O— or —Si(CH$_3$)$_2$ and/or
  - b2) one or more $CH_2$ groups can be replaced by —CH=CH—, —C≡C—, cyclopropane-1,2-diyl, 1,4-phenylene, 1,4-cyclohexylene or 1,3-cyclopentylene and/or
  - b3) one or more H atoms can be replaced by F and/or Cl and/or
  - b4) $R^5$ and $R^6$ together can also form a ring;
- c) phenyl, biphenyl, 1-naphthyl, 2-naphthyl, 2-thienyl, 2-furanyl;

$R^7$, $R^8$, $R^9$, $R^{10}$, $R^{11}$, $R^{12}$ are identical or different and are each
- a) hydrogen, —CN, —F, $NO_2$ or —Cl
- b) a straight-chain or branched alkyl radical having from 1 to 20 carbon atoms, where
  - b1) one or more nonadjacent $CH_2$ groups can be replaced by —O—, —S—, —CO—O—, —O—CO—, —O—CO—O—, —$NR^5$ or —Si(CH$_3$)$_2$— and/or
  - b2) one or more $CH_2$ groups can be replaced by —CH=CH—, —C≡C—, cyclopropane-1,2-diyl, 1,4-phenylene, 1,4-cyclohexylene or 1,3-cyclopentylene and/or
  - b3) one or more H atoms can be replaced by F and/or Cl;
- c) phenyl, biphenyl, 1-naphthyl, 2-naphthyl, 2-thienyl, 2-furanyl, —O-phenyl, —O-biphenyl, —O-1-naphthyl, —O-2-naphthyl, —O-2-thienyl, —O-2-furanyl, m, n, p, q, r are in each case identical or different and are 0, 1, 2, 3, 4, 5 or 6, with the exception of the compounds of the formula

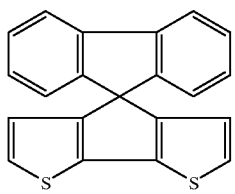

and also of 4,5-diazospirobifluorene and 4,4',5,5'-tetraazospirobifluorene.

2. A spiro compound of the formula (I) in claim 1, wherein:
- a) $X^{1-4}$ are identical or
- b) $X^1$ is identical to $X^2$ and $X^3$ is identical to $X^4$.

3. A spiro compound as claimed in claim 1, selected from the group consisting of

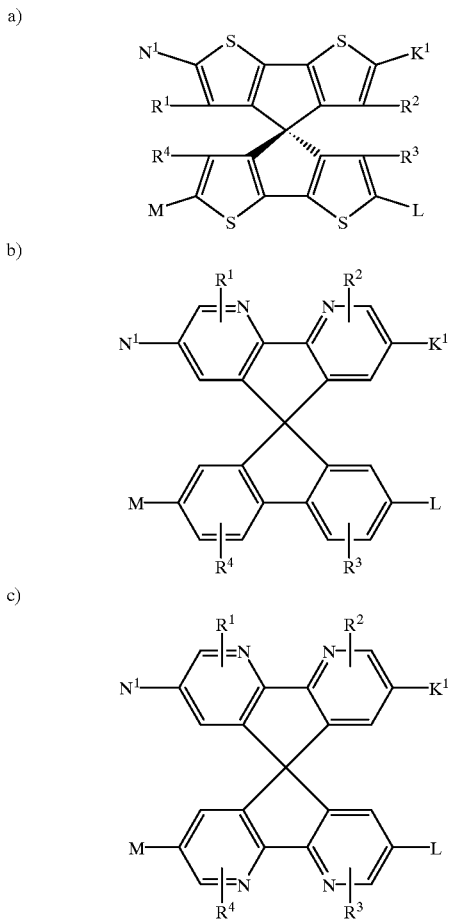

4. A charge transport material which comprises one or more spiro compounds of the formula

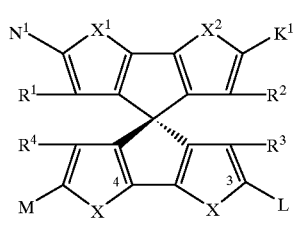

(I)

where the symbols have the following meanings:
$X^1$, $X^2$, $X^3$, $X^4$ are identical or different and are —S—, —O—, —$NR^5$—, —$CR^5$=N—, —$CR^5$=CH—, with the proviso that at least one of the groups $X^{1-4}$ is different from —$CR^5$=CH—;

$K^1$, L, M, $N^1$, $R^1$, $R^2$, $R^3$, $R^4$ are identical or different and are each
- a) hydrogen, —$NO_2$, —CN, —F or —Cl,
- b) a straight-chain or branched alkyl radical having from 1 to 20 carbon atoms, where
  - b1) one or more nonadjacent $CH_2$ groups can be replaced by —O—, —S—, —CO—O—, —O—CO—, —O—CO—O—, $NR^5$ or —Si(CH$_3$)$_2$— and/or
  - b2) one or more $CH_2$ groups can be replaced by —CH=CH—, —C≡C—, 1,4-phenylene, 1,4-cyclohexylene or 1,3-cyclopentylene and/or b3) one or more H atoms can be replaced by F and/or Cl and/or
c) one of the following groups:
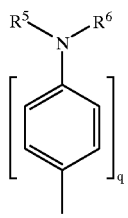
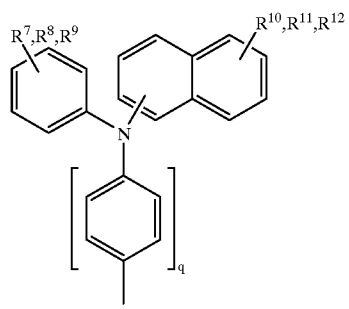
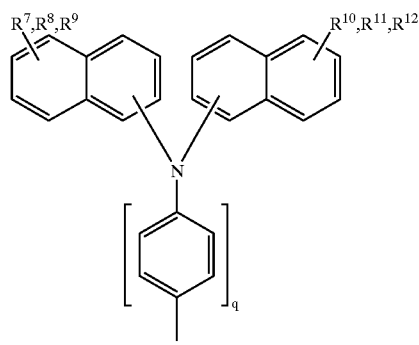
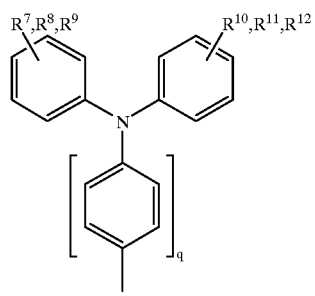
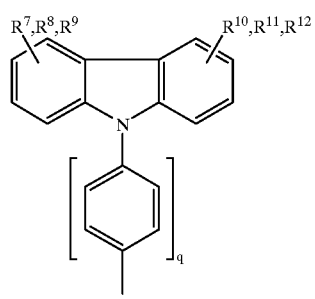
-continued
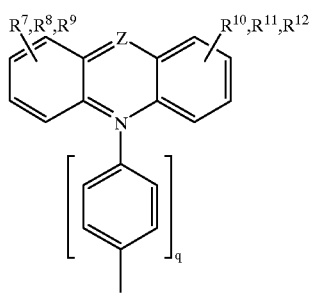
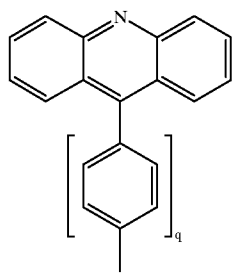
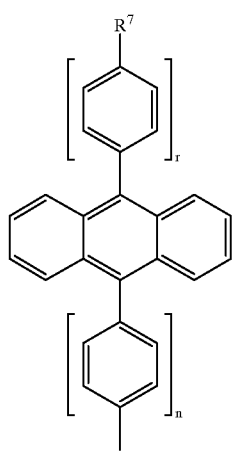
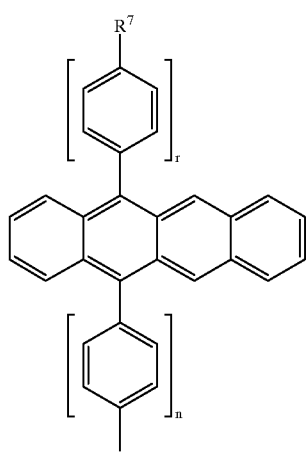

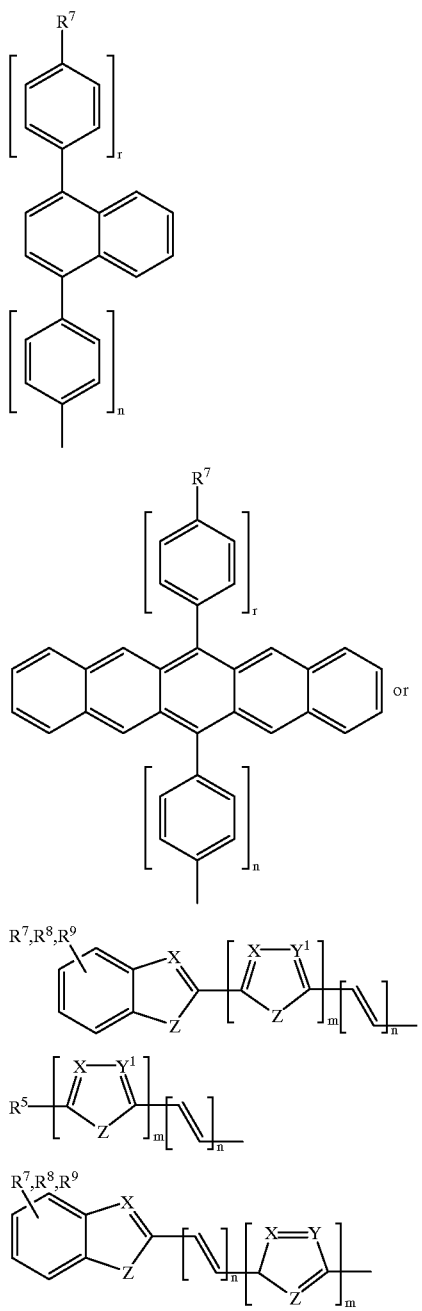

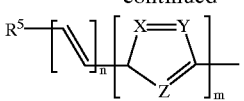

X, $Y^1$ are in each case identical or different and are =$CR^7$— or =N—;

Z is —O—, —S—, —$NR^5$—, —CRR—, —CR=CR— or —CR=N—;

$R^5$, $R^6$ are in each case identical or different and are each
a) hydrogen
b) a straight-chain or branched alkyl radical having from 1 to 20 carbon atoms, where
b1) one or more nonadjacent $CH_2$ groups which are not bound to nitrogen can be replaced by —O—, —S—, —CO—O—, —O—CO—; —O—CO—O— or —Si$(CH_3)_2$ and/or
b2) one or more $CH_2$ groups can be replaced by —CH=CH—, —C≡C—, cyclopropane-1,2-diyl, 1,4-phenylene, 1,4-cyclohexylene or 1,3-cyclopentylene and/or
b3) one or more H atoms can be replaced by F and/or Cl and/or
b4) $R^5$ and $R^6$ together can also form a ring;
c) phenyl, biphenyl, 1-naphthyl, 2-naphthyl, 2-thienyl, 2-furanyl;

$R^7, R^8, R^9, R^{10}, R^{11}, R^{12}$ are identical or different and are each
a) hydrogen, —CN, —F, $NO_2$ or —Cl
b) a straight-chain or branched alkyl radical having from 1 to 20 carbon atoms, where
b1) one or more nonadjacent $CH_2$ groups can be replaced by —O—, —S—, —CO—O—, —O—CO—, —O—CO—O—, —$NR^5$ or —Si$(CH_3)_2$— and/or
b2) one or more $CH_2$ groups can be replaced by —CH=CH—, —C≡C—, cyclopropane-1,2-diyl, 1,4-phenylene, 1,4-cyclohexylene or 1,3-cyclopentylene and/or
b3) one or more H atoms can be replaced by F and/or Cl;
c) phenyl, biphenyl, 1-naphthyl, 2-naphthyl, 2-thienyl, 2-furanyl, —O-phenyl, —O-biphenyl, —O-1-naphthyl, —O-2-naphthyl, —O-2-thienyl, —O-2-furanyl, m, n, p, q, r are in each case identical or different and are 0, 1, 2, 3, 4, 5 or 6.

5. A photovoltaic cell which comprise a change transport layer comprising one or more charge transport materials as claimed in claim 4.

* * * * *